(12) United States Patent
Colley et al.

(10) Patent No.: US 10,321,829 B2
(45) Date of Patent: Jun. 18, 2019

(54) MEASURING CHRONIC STRESS

(71) Applicant: JouZen Oy, Oulu (FI)

(72) Inventors: Ashley Colley, Oulu P (FI); Kari Juha Aulis Kivelä, Helsinki (FI); Markku Olavi Koskela, Oulu (FI); Marko Petteri Lahtela, Jääli (FI); Juuso Samuel Nissilä, Ii (FI)

(73) Assignee: JOUZEN OY, Oulu (FI)

( * ) Notice: Subject to any disclaimer, the term of this patent is extended or adjusted under 35 U.S.C. 154(b) by 694 days.

(21) Appl. No.: 14/143,937

(22) Filed: Dec. 30, 2013

(65) Prior Publication Data

US 2015/0182129 A1 Jul. 2, 2015

(51) Int. Cl.
| | |
|---|---|
| A61B 5/00 | (2006.01) |
| A61B 5/11 | (2006.01) |
| A61B 5/16 | (2006.01) |
| A61B 5/024 | (2006.01) |
| A61B 5/0205 | (2006.01) |
| A61B 5/0245 | (2006.01) |
| A61B 5/0402 | (2006.01) |
| A61B 5/0404 | (2006.01) |

(52) U.S. Cl.
CPC ........ *A61B 5/0205* (2013.01); *A61B 5/02405* (2013.01); *A61B 5/02416* (2013.01); *A61B 5/02438* (2013.01); *A61B 5/0402* (2013.01); *A61B 5/1118* (2013.01); *A61B 5/1126* (2013.01); *A61B 5/165* (2013.01); *A61B 5/4035* (2013.01); *A61B 5/4884* (2013.01); *A61B 5/6826* (2013.01); *A61B 5/7278* (2013.01); *A61B 5/7282* (2013.01); *A61B 5/746* (2013.01); *A61B 5/0002* (2013.01); *A61B 5/0059* (2013.01); *A61B 5/0245* (2013.01); *A61B 5/0404* (2013.01); *A61B 2562/0219* (2013.01)

(58) Field of Classification Search
CPC .......................... A61B 5/0205; A61B 5/4076
See application file for complete search history.

(56) References Cited

U.S. PATENT DOCUMENTS

| | | | | |
|---|---|---|---|---|
| 6,038,388 | A * | 3/2000 | Hogden | G06F 17/18 703/2 |
| 6,662,032 | B1* | 12/2003 | Gavish | A61B 5/1135 600/300 |
| 7,413,546 | B2* | 8/2008 | Agutter | A61B 5/00 600/485 |

(Continued)

FOREIGN PATENT DOCUMENTS

| | | |
|---|---|---|
| WO | 9817172 A | 4/1998 |
| WO | 2011109716 A2 | 9/2011 |

*Primary Examiner* — Christopher Koharski
*Assistant Examiner* — Amanda L Steinberg
(74) *Attorney, Agent, or Firm* — MP Patents, LLC

(57) ABSTRACT

A method for measuring stress based on the heart rate (HR), the heart rate variability (HRV), and the activity level of a user includes recording the HR, the HRV, and the activity level of a user at various times during the day. Thereafter, the three values are correlated to arrive at a stress level of the user. The stress level is estimated based on a predetermined set of algorithms and analysis methods. The physical disposition and the activity levels of the user are automatically detected and the vital parameters, i.e., the HR and the HRV recorded at times that are deemed fit for conducting orthostatic tests.

20 Claims, 16 Drawing Sheets

(56) References Cited

U.S. PATENT DOCUMENTS

| | | | |
|---|---|---|---|
| 2004/0116784 A1* | 6/2004 | Gavish | A61B 5/0205 600/300 |
| 2006/0224073 A1 | 10/2006 | Lin et al. | |
| 2010/0235181 A1* | 9/2010 | Loser | G06F 19/345 705/2 |
| 2010/0298677 A1 | 11/2010 | Lu et al. | |
| 2012/0071731 A1 | 3/2012 | Gottesman | |
| 2012/0083705 A1* | 4/2012 | Yuen | A61B 5/0002 600/508 |
| 2012/0245439 A1 | 9/2012 | Andre et al. | |
| 2012/0289789 A1* | 11/2012 | Jain | A61B 5/0022 600/301 |
| 2015/0230756 A1* | 8/2015 | Luna | A61B 5/721 600/484 |

\* cited by examiner

MEASURING CHRONIC STRESS

TECHNICAL FIELD

The present disclosure relates to a medical or wellness apparatus, in particular to methods and apparatus for dynamically measuring instantaneous balance between sympathetic and vagal nerve activities i.e. sympatho-vagal balance and modulation via heart rate (HR) and heart rate variability (HRV) in everyday activities or measurable life events to discover stress reactions and balance, or distress imbalance of a user.

BACKGROUND

The cardiovascular system is mostly controlled by the autonomic nervous system (ANS) through complex interplay between the vagal and sympathetic divisions (Guyton and Hall 2006). The ANS establishes and maintains a dynamic adaptive state, allowing an organism to respond to internal and external demands. It mediates changes in HR, blood pressure and peripheral vascular tone in response to daily challenges, including change of posture and physical exercise. A large body of evidence has shown that the functioning of the ANS plays a substantial role in cardiovascular health and disease (e.g. Rosenwinkel et al. 2001; Carter et al. 2003; Harris and Matthews 2004)

One model of stress was developed by Folkman et al. (1986) which identifies two processes: cognitive appraisal and coping. When faced with a possibly hazardous encounter with the environment, the person will go through the process of cognitive appraisal, evaluating the possible outcome of this encounter. Coping is defined here as the process of dealing with stress, in which the person changes the environment or her own internal expectations in order for these to match, or for the environment to exceed her expectations.

Stress is the body's multi-system response to any challenge that overwhelms, or is judged likely to overwhelm, selective homeostatic response mechanisms (Trevor A Day 2005). According to Lazarus, stress is defined as an internal process that occurs when a person is faced with a demand that is perceived to exceed the resources available to effectively respond to it, and where failure to effectively deal with the demand has important undesirable consequences (Lazarus et al, 1984). When under stress, the body responds in a way similar to how it responds to danger. Fatigue, being generally ill and feeling jittery are all sensations of stress (Selye, 1984).

One framework for studying stress is the Demand-Control-Support model (Karasek & Theorell 1990). This model, created with a focus on work-related stress, examines the relationship between the individual and the environment, from the point of view of the individual. Karasek & Theorell propose three factors to define the perception of the work environment: demand, control and support. Demand is the amount of workload placed on the person. Control refers to autonomy i.e. whether the individual is able to decide how to complete the work tasks or not. Support is defined as the amount of assistance that the worker gets from the manager or supervisor. This model is important in the context of research in effects of long-term stress (SALTSA 2006). Individuals with high demand, low control and low support usually experience prolonged periods of stress (Karasek & Theorell 1990).

A stress experience can be measured using three methods: evaluating the stimuli, evaluating the subjective cognitive response (by asking the subject how he feels) or evaluating the physiological bodily responses. The first method can obviously only be applied with humans and can potentially be deceiving because it does not take into account the capabilities of the subject to deal with the stressor. The second measurement method can be very subjective (Ursin & Eriksen 2004). Both are normally difficult to measure in real-time.

There are two primary physiological stress reaction systems: The hypothalamus-pituitary-adrenal (HPA) system and the autonomic nervous system (ANS). HPA and ANS play key roles in mediating this multisystem response. The ANS, including both the parasympathetic and sympathetic pathways, is highly responsible for this regulation of homeostasis (Porges 1992). Prolonged stress response may manifest itself in three forms: anticipatory responses to potential stressors, slow recovery from stressors, and/or recurrent activity related to past stressors (Brosschot et al. 2005).

The human stress response involves a complex signaling pathway among neurons and somatic cells. The internal environment of the body is regulated by two control systems: neuronal and hormonal (Jänig 2003). In stress research, two hormonal axes are often referred to: sympathetic-adrenal-medullary axis and hypothalamic-pituitary-adrenocortical (HPA) axis. Both of these axes involve adrenal glands, the medulla in former and the cortex in latter. The medulla is activated by the sympathetic branch of the ANS and its products are adrenaline and noradrenaline, common catecholamines. The product of the cortex is a group of hormones known as the corticosteroids, and perhaps the most important of these is cortisol. The HPA axis comprises the system of feedback interactions among the hypothalamus, pituitary gland, and adrenal glands. The HPA axis is a major part of the neuroendocrine system that controls reactions to stress and regulates many body processes, including digestion, the immune system, mood and emotions, sexuality and energy storage and expenditure.

Neuronal regulation acts rapidly and is mediated by the ANS. ANS is a part of the nervous system composed by a complex net of nerves that are distributed throughout the body and directly control the function of most tissues and organs. The ANS is mostly responsible for involuntary and non-conscious functions like regulating the HR, blood pressure, respiration, sweating and the like. Hormonal regulation is in general slower than the neuronal regulation (Jänig 2003). Both ANS and HPA work in conjunction to maintain the body in an equilibrium situation, also known as homeostasis, a concept created in 1865 by Claude Bernard that can be described as a slow regulatory process that operates on an organism, maintaining it in a stable condition (Cannon 1932).

A concept of allostasis defined by Sterling & Eyer (1988) is similar to homeostasis but it works faster. It responds to rapid changes in the environment, such as exposure to a pathogenic (e.g. virus or bacteria), or a prolonged "fight or flight" reaction. Every time there is a stress response, the organism enters a state of arousal and each internal system responds to adapt to the change. This response starts in the brain, with the activation of the Sympathetic system and deactivation of the Parasympathetic system from the ANS occurring in parallel with a release of hormones in the HPA. This response has short-term benefits as it adapts the organism to the environment. However, it does not come without long-term consequences. Either because of inefficient responses or repeated exposure to stressors, allostasis has a long-term effect on the body called allostatic load.

Further, McEwen & Wingfield (2003) define two types of allostatic load:

Type 1 allostatic overload occurs when energy demand exceeds supply, resulting in activation of the emergency life history stage. This serves to direct the animal away from normal life history stages into a survival mode that decreases allostatic load and regains positive energy balance. The normal life cycle can be resumed when the perturbation passes. Type 2 allostatic overload begins when there is sufficient or even excess energy consumption accompanied by social conflict and other types of social dysfunction. The latter is the case in human society and certain situations affecting animals in captivity. If allostatic load is chronically high, then pathologies develop. Type 2 allostatic overload does not trigger an escape response, and can only be counteracted through learning and changes in the social structure.

Various studies show that allostatic load can lead to permanent changes in immunological, cardiovascular and neuronal systems. Stress has been associated with infections and inflammations, cardiovascular, pulmonary, dermatological and immunitary diseases, diabetes, obesity, psychiatric conditions, and progression to cancer (e.g., Seeman et al. 1997, McEwen 1998, McEwen & Wingfield 2003, Kaplan et al. 1991, Yun & Doux 2007). Increased cardiovascular risk seems to be related with over activity of the Sympathetic nervous system (Julius 1993), due to frequent activation in stress responses. It has been shown that stress impairs the homeostatic regulations of the body, particularly the cardiovascular regulation (Mezzacappa et al. 2001, Lucini et al. 2005). The reduced autonomic regulation of the heart makes it more vulnerable to acute stress (i.e. stress happening during short periods of time), where short term rises in HR and blood pressure can cause arrhythmia and sudden death (Lucini et al. 2005).

Both the sympathetic branch of the ANS and the HPA axis are activated during the acute stress. Chronic and/or unpredictable activation of these stress response systems can lead to a diminished capability to respond appropriately. Increased activation of the HPA axis and that of the sympathetic nervous system are frequently reported in depressed and anxious patients.

The phenomenon of beat-to-beat fluctuation of HR has been termed respiratory sinus arrhythmia. During recent decades, a variety of HRV methods have been developed and their ability to evaluate the cardiac autonomic modulation has been proven in multiple situations, as well as under influence of different stressors. The measurement of HRV provides a non-invasive tool for assessing autonomic HR control.

HRV is a term used to describe the variations in time-intervals between heart beats, i.e. variations in electrocardiographic R-to-R peak interval (RRI) lengths. HRV is primarily due to the changing modulations of vagal and sympathetic control of the heart and may therefore be considered as an estimate of autonomic HR control. Methods for detecting beats can be: Electrocardiography (ECG), blood pressure, ballistocardiograms, and the pulse wave signal derived from a photoplethysmograph (PPG). Detection of beat-to-beat interval and subsequent measurement of the HRV can also be performed by optical measurement using infra-red light emitting diodes (LED)'s. IR LED's are used to measure either transmittance or reflectance of light through body tissue such as tip of the finger or ear lobe or elsewhere on the body.

Finger plethysmography (FPG) is a simple, noninvasive, well-known method for monitoring peripheral circulation. Peripheral blood vessels contain a high concentration of arteriovenous anastomosis, innervated by alpha-adrenergic nerve fibers. Peripheral blood flow thus reflects ANS activity, which is commonly known as one indicator of mental stress. Although indices of ANS activity are usually calculated using HRV, a number of recent reports have noted that finger pulse rate variability has nearly the same physiological function as HRV. Because measurement of HRV usually requires electrodes to be attached to the chest or stomach, and electrodes sometime pick up noise from body movements, FPG is a superior method of measuring acute mental stress. It is a minimum burden on user and it can accurately measure changes in peripheral blood flow. Furthermore, it has been proposed that the FPG waveform reflects health conditions, with the signal becoming simpler and weaker as a result of disease or aging. Studies show that peripheral arterial vasoconstriction induced by mental stress predicts stress-induced myocardial ischemia. Also acute mental stress will lead to sympathetic nervous system activation and consequent peripheral vasoconstriction. Chronic stress may lead to peripheral blood ischemia and, consequently, cardiovascular disease. Measuring FPG during stress is important as a means of predicting health outcomes.

A modified HRV has been proven to be associated with medical conditions such as acute and chronic stress, recovery from stress or physical loading, congestive heart failure, diabetic neuropathy, depression, post-cardiac transplant, and poor survival in premature babies. HRV is a key marker of autonomic dysfunction and the effects seen through it are immediate, while blood pressure, baroreflex, and therapeutic effects are delayed. This is consistent with data on the relationship among stress, HPA axis activity, and brain function.

The effects of stress and recovery influence the resources of the ANS. Under optimal conditions, the autonomic resources are fully recovered and mainly vagal resources are needed. Typically however, the resources are not fully recovered, but there is no risk of problems in case of disposition to stress. If the resources are low, the risk of problems in autonomic modulation increases, as the sympathetic activation is increased already during rest. In the case of chronic exhaustion the resources are very small, and mainly sympathetic.

The tenth cranial or vagus nerve is responsible for the vagal (parasympathetic) modulation of heart (Hainsworth 1998). Activity in the vagal nerves slows the HR by slowing the rate of spontaneous depolarization of pacemaker cells. At rest, HR decreases from the intrinsic value of 110-120 bpm to 60-80 bpm by the predominance of vagal activity over sympathetic activity. The balance between vagal and sympathetic activity is responsible for adjusting the HR. HR values lower than the intrinsic values indicate vagal predominance while HR values over intrinsic values reflect sympathetic predominance (Hainsworth 1998).

Increase in sympathetic activity increases HR by increasing the rate of depolarization of pacemaker cells. Whereas vagal activity can delay the very next heart beat, sympathetic responses are much slower. Maximal responses may not occur for as long as 20-30 seconds. Similarly to the vagal effects, the interval between depolarizations, R to R interval (RRI) is more closely related to the frequency of sympathetic stimulus. High sympathetic drive is responsible for the high HRs seen during maximal exercise, also increasing the force of contraction and shortening the duration of systole.

Decreased vagal function and HRV are shown to be associated with increased fasting glucose and hemoglobin A1c levels, increased overnight urinary cortisol, and increased proinflammatory cytokines and acute-phase proteins. All of these factors have been associated with increased allostatic load and poor health. Thus, vagal activity appears to play an inhibitory function in the regulation of allostatic systems. The prefrontal cortex and the amygdala are important central nervous system structures linked to the regulation of these allostatic systems via the vagus nerve.

While the changes in e.g. blood pressure and HR are the result of combined changes in parasympathetic and sympathetic nervous system (PNS and SNS respectively), HRV indicates individual contributions of PNS and SNS. Beat-to-beat variability in HR or "instantaneous HR" is governed by modulations in SNS and PNS activity. HR oscillates with many frequencies that reflects the influence of different blood pressure systems: rapid fluctuations (HF, 0.4-0.15 Hz) are caused by vagal activity, slow fluctuations (LF, 0.15-0.04 Hz) are caused by a mixture of sympathetic and vagal activity, slower fluctuations are caused by even slower regulatory systems (e.g. temperature fluctuations, day-night periodicity).

HRV is most commonly analyzed with time domain and conventional frequency domain methods. Time domain analysis can be easily calculated with simple statistical methods. The simplest index is the standard deviation of the RRIs over the selected period (SDNN). Frequency domain analysis decomposes the RRI data into its frequency components and quantifies them in their relative intensity, termed power. It provides information how overall HRV is distributed as a function of frequency. E.g. nonparametric Fast Fourier Transformation and parametric autoregressive modeling are used. The advantages of the nonparametric methods are the simplicity of the algorithm and high processing speed, while the advantages of parametric methods are smoother spectral components, simple post-processing with an automatic calculation of different components and an accurate estimation of power spectral density, even on small number of samples.

HRV has classically been used to assess autonomic HR control at rest. A conventional frequency domain analysis of HRV has been developed essentially for conditions in which the level of HR is unchanged. Recently, studies have been targeted at developing novel methods of HRV analysis that allow the assessment of HRV also in conditions when HR changes rapidly. By using time-frequency approaches it is possible to obtain information on autonomic control when HR changes rapidly. Time-frequency analysis and a short-time Fourier transform (STFT) method allows HRV also to be assessed from non-stationary signals. This is a major advantage, since autonomic HR control is characterized by transient changes.

Most real-life challenges induce a rapid increase or decrease in HR. It has been recognized that transient changes in HR in response to variety of tasks reveal important information on the functioning of the ANS. In order to obtain information on autonomic control during strongly time-dependent phases of an intervention, several tools for time-frequency analysis have been applied to RRI data. The advantages of the STFT method are computational efficiency, simple implementation and automaticity. It can also be seen as an objective method as after the selection of window length and frequency ranges no further decisions are needed. The STFT method calculates consecutive power spectra of short portions (of constant duration) of the signal and thus informs about changes in the power spectrum as a function of time.

Measuring the sympatho-vagal balance utilising HR and HRV offers deep understanding of dynamic, autonomic interrelations in humans in totally noninvasive, unobtrusive means. When instantaneous balance between sympathetic and vagal nerve activities i.e. sympathovagal balance and modulation are measured dynamically in every day measurable life events it is possible to generate great understanding and long term view and trend on the persons bodily reactions in different daily life situations.

When combined and correlated with the measurement of activity i.e., the measured level of physical provocation or non-provocation (i.e., the situation where there is not physical activity e.g., mental load or pressure) it is possible to create multidimensional view on the personal healthy area in the context of ANS reactions in ratio to the activity level of the user in different measurable situations.

In addition to associations with age, gender and physical fitness, several studies show great inter-individual variation in HRV indices. It should also be noted that heritable factors may explain a substantial proportion of variation in HR and HRV. HRV indices, with the exception of the LF/HF ratio, are independent of body position and rather stable when repeated on the same day, and they should be used when studying long-term observations of autonomic measurements in healthy subjects.

Stressful conditions and prolonged exposure to stress can manifest themselves into a number of emotional, cognitive, physiological and somatic symptoms (Melamed et al., 2006). There are a large number of investigations dealing with HRV during exposure to standardized psychological stressors such as mental arithmetic. Vagal modulation of the heart appears to be sensitive to recent experiences of persistent emotional stress regardless of age, gender, respiration rate or cardio-respiratory fitness. Chronic work stress (high effort-low reward) has been associated to low HRV during work, leisure and sleep both during work days and weekends. Psychosocial stress symptoms during the workday may not be harmful for the health, but if prolonged, they may lead to cardiovascular disease.

In recent years, laboratory research on mental workload and stress reactivity has shown that certain psychologically relevant measurable biochemical and physiological indices provide additional measures to assess and monitor our adaptation resources. When these bodily reactions are evaluated in real-life conditions as well, it offers a useful way of examining one's reactions to stress and recovery in more practical settings. Vagal modulation of heart appears to be sensitive to recent experiences of persistent emotional stress regardless of age, gender, respiration rate or cardiorespiratory fitness. The results of academic studies have shown that higher incidence of stress symptoms are significantly associated with lower HRV in the orthostatic test regardless of age and gender. Also it has been shown that HRV measurements are useful tools in analyzing stress in real-life conditions together with subjective evaluations of stress.

Stress results primarily from unmanaged emotions. Factors such as anxiety, worry or fear are disablers of performance. States of peak performance have a measurable physiological correlate. A physiological state characterized by improved and coherent heart rhythm leads to measurable improvement in mental and cognitive performance, including heightened decision-making. Different emotions, e.g. levels of hostility have been shown to affect HRV. Different techniques that engender positive thought processes in individuals have been demonstrated to produce a significant improvement in HRV. Emotions such as hostility and anger produce a sympathetically dominated HRV, whereas feelings of appreciation shift the HRV power spectrum in the opposite direction. It has been shown that people who express positive emotions show less life stress and are less likely to become ill.

A physiological state of entrainment, where HRV patterns, brain activity and respiration synchronize with each other, correlates with a state of peak performance. This same state is also associated with a reduction in stress-related symptoms, including tachycardia, tension and various aches and pains. These positive effects are best achieved during conditions of positive emotional management. There is now increasing evidence that the physical symptoms of stress are linked negatively to workplace effectiveness. Techniques that improve HRV in individuals have been shown to benefit organizations by increasing productivity, reducing health care costs, lowering absenteeism and improving retention. Also studies have shown that executives with stage 1 and 2 hypertension have been able to restore their blood pressure to normal without medication, by learning techniques that regulate their HRV.

The role of mood, emotions and thought processes (positivity and negativity) are often ignored or placed in the background when addressing an individual's well-being and recovery process. More recent research, particularly involving HRV, is demonstrating the profound potential gain that can be achieved on the basic physiological regulatory processes that govern health by addressing an individual's emotional response and employing simple techniques to alter the negative thought processes that affect our responses to challenge and stress. HRV is a great tool by which we can examine the interface and coherence between mind and body. An ability to control HRV could well alleviate negative mood states in people seeking assistance for inadequate stress responses, anxiety or depression. Since there is a clear association between negative mood states and heart disease, the efficacy of any psychological intervention to reduce the risk of heart disease would be improved if it focused directly on improving ANS imbalance characterized by SNS dominance and low HRV. Also, since an increasing number of physical ailments appear to be associated with ANS imbalance the potential application of HRV to monitor this balance is enormous.

In addition to the passive head-up tilt, the Active Orthostatic Task (AOT) is a simple non-invasive test that provokes well-documented abrupt cardiovascular changes, eliciting a fast response in the different divisions of the autonomic nervous system. For example, unaided standing up after sitting down for some time (for a few minutes) and remaining standing for a short time (e.g., 1 min) is an AOT. This kind of an AOT results in a shift of blood away from the chest to the venous system below the diaphragm, and thus arterial blood pressure decreases rapidly. In normal subjects, compensatory mechanisms are activated immediately after standing-up in order to maintain arterial blood pressure at an appropriate level of perfusion for all the vital organs, especially the brain. The initial adjustments to standing-up are primarily mediated by the autonomic nervous system, and the humoral regulatory system only becomes involved during prolonged standing. Studies show that the fast and slow cardiac response to the AOT seems to be mediated by the vagal system alone. An example of the opposite kind of AOT is sitting down after standing or walking. The short-time Fourier transform (STFT) method to analyze HRV data is successfully used to detect vagal response to the AOT.

HR and HRV measured as a part of orthostatic tests can be used to predict with high level of accuracy the chronic stress that a person is going through. Orthostatic tests include measuring various vital parameters of the body while the person is supine or sitting and relaxed for several minutes and while person stands up and is standing in an upright position for some time. The change from lying to standing position creates redistribution of blood volume. Systolic blood pressure decreases and HR increases. The peak HR is found approximately 15 seconds after standing up. Being in a continued standing up position, HR starts to oscillate at a certain level. The orthostatic HR is the difference between the HRs at supine rest and at standing positions. For example, if the average HR in a lying position is 56 and at standing 80, the orthostatic HR is 24 beats per minute (bpm).

However, many different stages can be used to measure the standing HR. For example, few health care providers prefer using the peak HR after the person stands up and others prefer using the average HR after the HR has peaked. The peak HR is usually interpreted to reflect parasympathetic nervous activity and the average HR to reflect sympathetic activity, although both these parameters are indicators of disturbances in ANS.

Since precise instructions for performing the orthostatic test do not exist, the patients are typically advised to decide a practice for themselves and then perform the test always the same way. Therefore, to perform the test the person needs to especially designate a time during the day when he has to remain in a supine or sitting position for X minutes and measure the resting HR. Thereafter, he/she has to stand up and then measure the average HR or the peak HR as advised.

Several measurements of the orthostatic HR need to be performed at plurality of times in a day over a period of several days before a stress level can be derived conclusively. Thus, orthostatic HR measurement may prove to be a tedious task for working professionals having busy work schedules. The cumbersome measurement procedure ultimately leads to missed test readings or tests performed without following the protocol properly, thereby resulting in inconclusiveness of the readings obtained.

SUMMARY

According to a first aspect of the present disclosure, there is provided a method for measuring stress which includes measuring a HR component, a HRV component and an activity level component with an assessment system at a plurality of times. The activity level, HR and HRV components measured at the plurality of times are compared mutually to determine whether the measured values are predetermined relationships. A deviation from the normal relationship signals a possibility of stress experienced by a user. The measured values of activity level, HR and HRV components are composed into a plurality of corresponding stress levels and an acceptable stress space from the plurality of stress levels is defined. Subsequently, a prompt is provided when a stress level lies outside of the acceptable stress space.

The method for measuring stress may also include receiving user input regarding the user's disposition and correlating this input regarding the disposition with stress levels.

According to a second aspect of the disclosure, there is provided a method for measuring stress which includes detecting activity level and measuring HR with a system configured for attachment to an exposed region of a body of a user. A provocation from detected activity level and measured HR is identified. HRs before, during and after the identified provocation are recorded. HRV and derived parameters from the recorded HRs are computed.

The method may include recording a biphasic HR response after the provocation. Identifying the provocation further includes measuring a high HR and detecting a low activity level and prompting a user for a disposition input when detected activity level is low and computed HR variability is low. A provocation is established as a training activity when measured HR is high and detected activity level is high.

According to a third aspect of the disclosure, there is provided a method for measuring stress which includes detecting provocations and measuring HR with a system configured for attachment to an exposed region of a body of a user. This method further includes computing HRV with a data processor by combining HR measured for a duration before a detected provocation with HR measured for a duration after the detected provocation and deriving a stress level rating using the computed HRV.

The method may include establishing provocation intensity for each detected provocation.

DESCRIPTION OF THE DIAGRAMS

Embodiments of the present disclosure will now be described, by way of example only, with reference to the following diagrams wherein.

Figure 1:
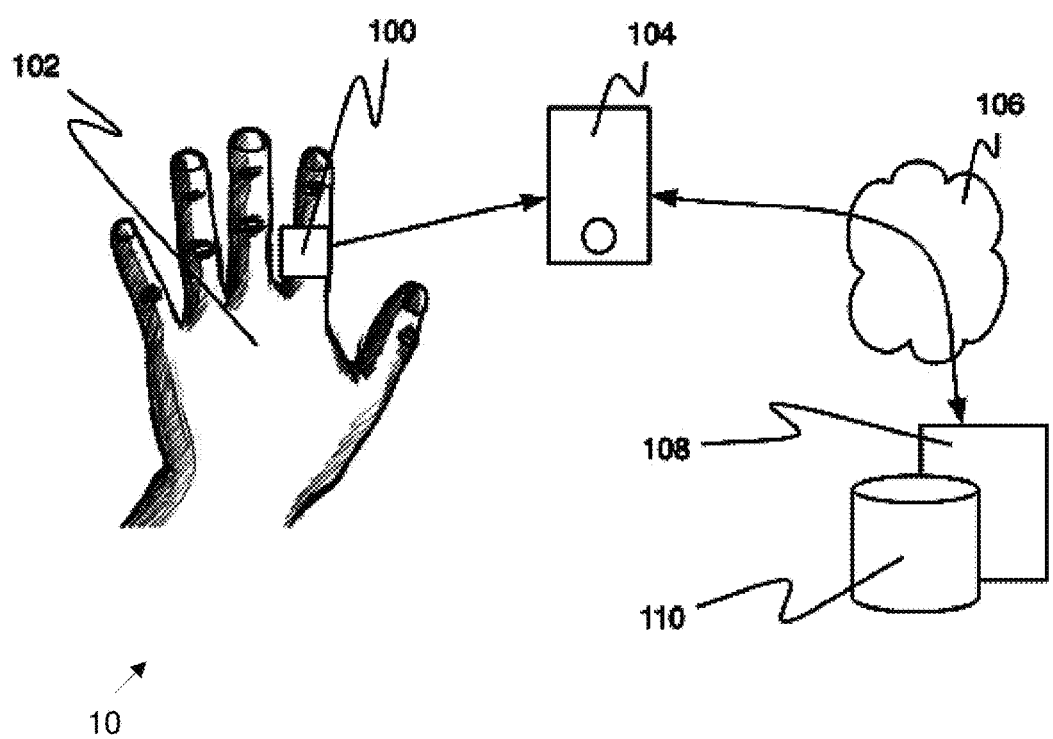
FIG. 1 is an illustration of an example apparatus for measuring orthostatic heart rate (HR)

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF THE EMBODIMENTS

In order to overcome limitations of conventional orthostatic HR and HRV measurement apparatus, the present disclosure provides for an apparatus for measuring orthostatic HR and HRV that is capable of performing the measurement of HR and HRV continuously without requiring the person to follow any measurement protocol. The apparatus is capable of deriving orthostatic HR and HRV by detecting the disposition of the user, of correlating various orthostatic HR and HRV measurements and is configured to convert the measured values into stress levels.

In order to collect HR and HRV data—both short term and long term—in different measurable real-life situations it is important that the manners, methods and apparatus used are simple, easy-to-use and allow for continuous measurement in case of interventions. Detection of static and provocative moments i.e., the transient changes in HR and sympathovagal resources in response to a variety of tasks is facilitated by automatic recognition of a user's activity and the strength of the provocation. Also, due to inter-individual variation of responses, a self-learning apparatus capable of measuring and mapping responses in the context of HR and/or HRV and/or correlated activity offers significant benefits. With such apparatus, reactions and responses of the sympathovagal resources may be measured in the spaces and relations of HR/activity, HR/HRV, HR/HRV/activity.

The disclosure further provides for a method of measuring stress based on the HR and/or the HRV, and/or the activity level and/or other sympato-vagal provocation, loading or a withdrawal of such of a user. The HR, the HRV, and the activity level or provocation, the withdrawal of provocation, the load of a user are recorded at various times during the day and the values are correlated to arrive at a stress level of the user. The stress level is estimated based on a predetermined set of algorithms and analysis methods. The physical disposition or sympato-vagal provocation and the activity levels of the user are automatically detected and the vital parameters, i.e., the HR and/or the HRV are recorded at times that are deemed fit for conducting orthostatic tests.

According to the protocol of orthostatic testing, vital parameters are recorded just prior to and just after a provocation. These measurements are repeated several times during the day to arrive at the baseline stress levels of the user and also to establish whether the user has chronic stress. The vital parameters used to establish baseline stress values can be utilized as a reference when adjusting any long term or occasional stress measure derived from any daily measurable moment consisting of HR, HRV, activity level, and symatovagal provocation data. Daily stress levels may be derived as a combination of HR and HRV, HRV and provocation, HR and activity level, HR and provocation, and provocation and activity.

Since measurements are performed by automatically detecting suitable time instants, the user does not need to sacrifice separate time to follow the instruction of performing orthostatic test. Sacrificing time can be particularly cumbersome if the tests need to be performed several times during the day and over several days. Thus, the user can go about with his/her daily work schedule and the stress levels faced by him/her continue to be automatically recorded and stored at a centralized database. Storage of the stress levels over several days enables medical practitioners to ascertain with a high degree of accuracy the current stress faced by the user and to also establish a trend in the stress levels of the user. This might prove helpful in prescribing diet, medicines, exercises etc. for the user. Identifying an incremental trend in the stress levels may contribute to the prevention of serious heart ailments. Further, acceptable stress levels are also established and any stress level that is outside the normal limits is flagged. While the orthostatic tests are being conducted, the user is asked to provide a feedback using his/her hands, fingers, etc. to aid an understanding of the kind of stress the user is going through. In a scenario when the user is experiencing abnormal levels of stress, a mobile phone application may be automatically initiated which, in turn, may call for medical assistance.

It will be appreciated that features of the disclosure are susceptible to being combined in any combination without departing from the scope of the disclosure as defined by the appended claims.

In FIG. 1, an example apparatus is indicated generally by 10. The apparatus 10 includes a measuring device 100 configured for fitting to a body part 102, a mobile terminal 104, a communication network 106, a server 108, and a database 110.

The measuring device 100 is attached to the body part 102 of a user for detecting a heart pulse of the user. In an embodiment of the present disclosure, the measuring device 100 uses optical electronics to measure a blood volume pulse (BVP) to detect the user's heart rate (HR). The body part 102 may be, for example, one of the hands of a user and the measuring device 100 may be attached to a finger, such as a forefinger, of the hand. Measuring device 100 may take the form of a ring. From the HR, the measuring device 100 calculates heart rate variability (HRV) as described subsequently. The measuring device 100 is capable of detecting one or more physiological signals generated by the user's body, and apparatus 10 is configured to correlate the physiological signals with the physical disposition of the user, and process the measured data to derive the physiological state of the user. The measured data may be sent to the mobile terminal 104 and from the mobile terminal 104 via communication network 106 to the server 108. The server 108 processes and analyses the measured data to output stress levels experienced by the user and stores the processed data in the database 110 for future comparisons. The measured data and the stress levels hence obtained may also be shown in the mobile terminal 104 or in any other device capable of presenting the results. In an embodiment of the present disclosure, a display screen may be interfaced with the measuring device 100 for displaying the measured data and the stress levels. Further, the server 108 is configured to send the measured data and the stress levels to the measuring device 100 via the mobile terminal 104.

In an example, the measured data may also be directly sent to a computer, a smart watch, other Bluetooth or wireless data transfer capable devices (not shown) or a combination of these. The measuring device 100 can also receive data and commands from the mobile terminal 104, a computer, a smart watch or other Bluetooth or other wireless data transfer method capable device (not shown) or a combination of these. The measuring device 100 is arranged to store processed and raw measurement data in a memory associated with the measuring device 100 and provides comparisons with historical data. The measuring device 100 is configured to show or otherwise present the measurement result and historical data as trend in a display (not shown) associated with the measuring device 100.

The measuring device 100 includes one or more sensors (not shown) arranged to detect the user's movement, and the relative strength of the movement (and posture). The HR of the user measured when the user is in different physical dispositions may be used to obtain orthostatic HR at a plurality of times during the day. For example, at a particular time of the day (i.e., early morning) the user may be in a relaxed supine position. The measuring device 100 measures the HR and, by the use of the one or more sensors mentioned above, also establishes that the user is in a relaxed supine position, i.e., without any provocation. Thereafter, when the user stands up or begins to perform any other activity, i.e., after the provocation, the measuring device 100 again measures the HR (an average HR or a peak HR may be measured) and also establishes that the user is in a standing-up position.

Subsequently, an orthostatic HR is calculated by subtracting the supine HR (before provocation) from the standing-up HR (subsequent to provocation). Further, the HRV is also calculated using the supine HR and the standing-up HR. The measuring device 100 includes one or more in-built algorithms which use the measuring device 100 to output stress level corresponding to the calculated HRV. The above exercise of measuring orthostatic HR and the HRV and related derivative parameters may be repeated several times during the day when the user is undergoing different levels of provocation and over a period of several days to establish autonomic nervous system (ANS) reactions. By combining the ANS reaction and the level of physical provocation in different situations the measuring device 100 detects the user's stress reactions and the level of acute and chronic stress. In an embodiment of the present disclosure, the duration of measurement of the HR or the count of heartbeats measured before and after the identified provocation is automatically adjusted by the measuring device 100.

The measuring device 100 also takes visual or haptic user input/feedback regarding the provocation detected. The measuring device 100 then applies sniffing logic on the feedback to establish an activity level for the provocation and to interpret the stress level accordingly. Visual feedback may be programmed according to preferences of the user. For example, a positive stress level due to exercise may be signaled by the user to the measuring device 100 with a figurative hand movement such as a 'thumbs-up' gesture. Similarly, a negative stress level experienced by the user due to a stressful meeting at work place may be signaled by a figurative hand movement such as a 'thumbs-down' gesture.

Figure 2:
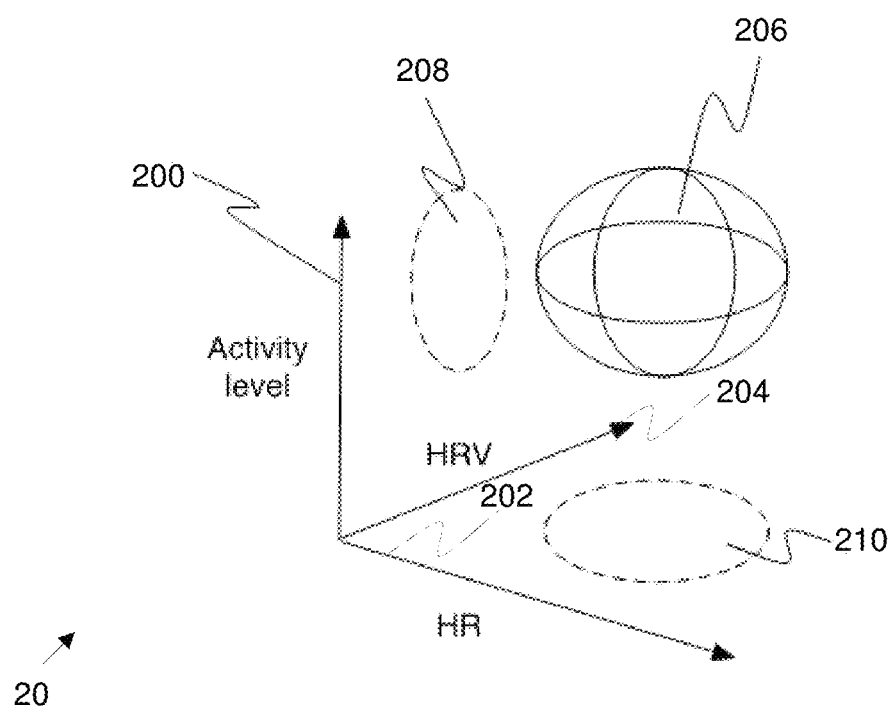
FIG. 2 is an illustration of an example three-dimensional (3D) axis system.

The measuring device 100 interprets the above gestures and the HRV estimates to arrive at a sensible estimate of stress level corresponding to the activity level. The measurement of stress levels at several times of the day when the user is performing different activities and correlating those stress levels with the user feedback enables the determination of a health space (FIG. 2). The health space provides the user with acceptable limits of stress level corresponding to predetermined physical activity and HRV values. Values of stress level, activity level, and HRV lying outside the health space are flagged by the measuring device 100.

In an example of the present disclosure, the one or more sensors in the measuring device 100 include at least one of an accelerometer, a gyroscope, and a magnetometer. The measuring device 100, with the use of the one or more sensors, automatically detects situations that apply as measurable and comparable physical provocations (e.g. when the user stands up, is climbing the stairs etc.) and situations where there is no physical provocation (the user is still or there is only minor movement).

In an example of the present disclosure, as a stand-alone device measuring device 100 has data processing power, built-in algorithms and other necessary capabilities to execute automated and dynamic orthostatic test procedures (either from supine to standing or from sitting to standing) to measure whole ANS functionality, i.e. sympathovagal resources (stress reactions vs. recovery). The device gives haptic and visual instructions to user during the execution of the orthostatic test to receive user inputs regarding the activity level and stress type that the user is experiencing. Additionally, the measuring device 100 has the capability of detecting the signal and measurement quality during the measurement procedure and therefore can dynamically adjust the necessary time needed for supine (or sitting) and standing periods respectively. Additionally the algorithms in the measuring device 100 enable inclusion of the effects of biphasic HR response subsequent to assuming the upright position in the analysis. HRV calculations m be performed throughout the test period.

Further, by virtue of acceleration sensors installed in measuring device 100, measuring device is capable of removing artifacts caused by movements of the user as well as measuring the strength of the provocation (standing up from supine position in this case). When the orthostatic test protocol is repeated several times over a long duration, measuring device 100 yields higher quality and more comparable results. Measuring device 100 is configured to collect, calculate and present trend information based on long data collected with repeated tests. The trend information provides a view of the manner in which the stress of the user has developed over time, the current level of stress, and the direction towards which the trend is developing.

In some embodiments, measurement device 100 can be attached to body parts other than a finger for example to a wrist, an ankle, a waist, an earlobe etc. Usage of measurement device 100 is described below in various scenarios.

Figure 3:
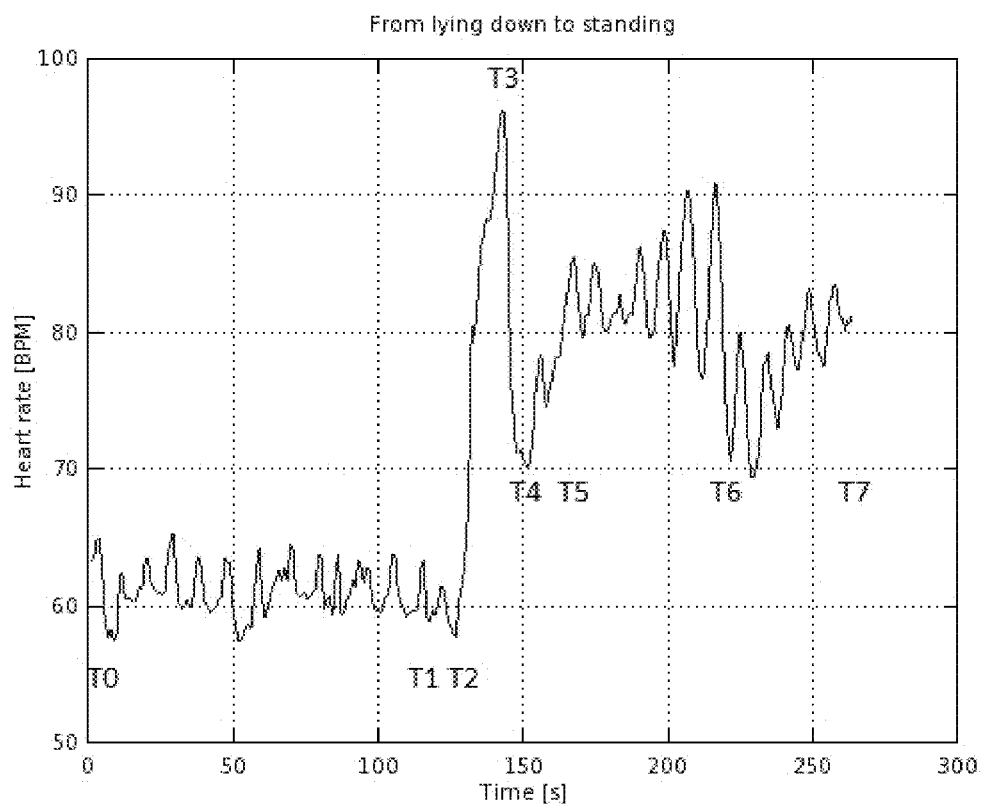
FIG. 3 is a graph of heart rate vs. time measured when a user transitions from lying down to standing.

In an example of orthostatic test measurement setup, a person uses measurement device 100 on his or her finger. While the person lies in bed in the morning after a night of sleep, the system begins measurement on T0 (FIG. 3). The system is configured to dynamically change the time needed for the measurement. For example, if pulse data quality is good measurement time can be shorter than in cases of poor measurement data quality (e.g., due to movement or other artifacts affecting measurement quality). After a sufficient amount of good quality data is collected, the user is prompted to stand up (stand up occurs at time T1). The person stands still and pulse data is measured until a sufficient amount of good quality data is collected. Again, as prior to standing up the time of measurement can be varied dynamically. The strength of physiological provocation/activity is measured during each phase with accelerometer.

Figure 4:
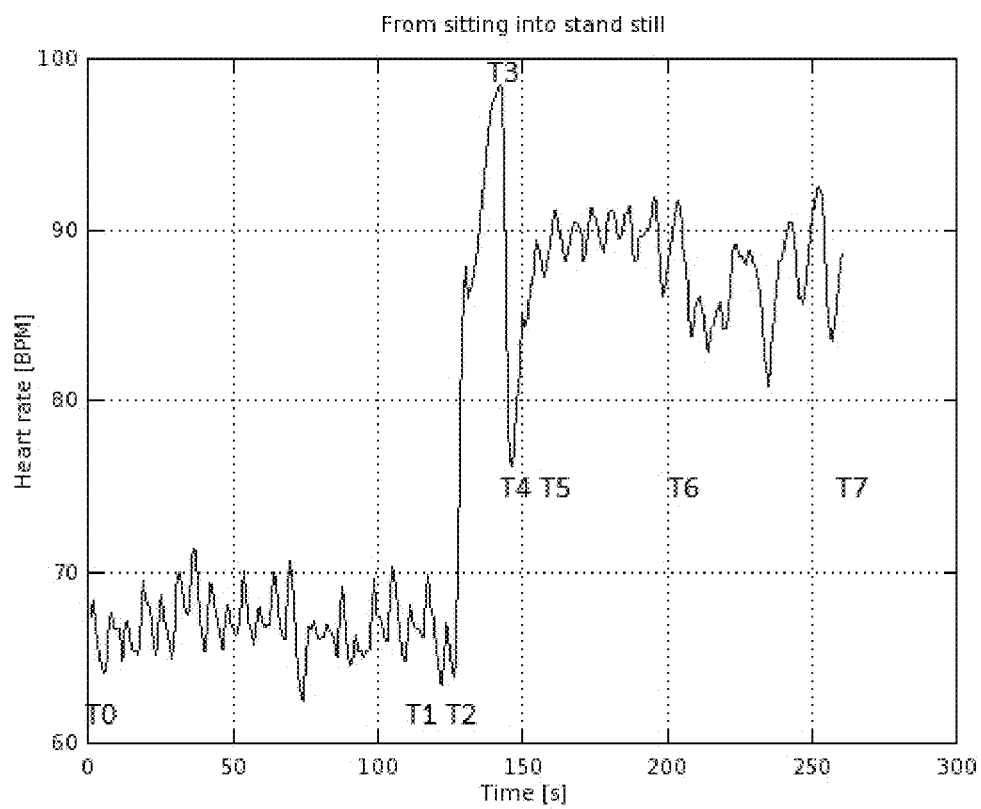
FIG. 4 is a graph of heart rate vs. time measured when a user transitions from sitting to standing still.

The test may also be performed from sitting to standing and the dynamic measurement applies the same way (FIG. 4).

The bodily reaction after stand up (starting from T2 i.e. after certain delay to the provocation i.e., standing up) is measured and analysed in each period i.e., T2 to T3, T3 to T4, T4 to T5, T5 to T6, T6 to Tn and Tn to Tn+1. The reactions of the autonomic nervous system are measured and analysed during each phase i.e., laying down, stand up and standing up. Both acute stress reaction and long term status of stress are analysed in ratio to the strength of provocation.

When repeated over time, the test results and analysis data in each phase indicate the trends on e.g., how stress is developing over time and whether or not recovery is happening. Additionally, each individual measurement may be compared to the long-term data to uncover potential abnormal or stressful situations.

When compared to an orthostatic test performed in a clinical setting by those of ordinary skill in the art, the device allows more a dynamic and time-saving method of performing an orthostatic test since the stand-alone device is arranged to monitor the quality of the measurement and pulse data in real-time and to adjust the length of the supine and standing phases accordingly. Additionally, the device measures the strength of the physiological provocation and ratio of the separate measurements to each other based on that to yield more comparable results. Further, it measures bodily reactions during transition (stand up) and after that but before the body is stabilised in the new homeostasis. The device is configured to execute analysis of the measurement and indicate results to the user. Additionally, it is capable of providing a long-term view based on long data collected during separate, repeated measurements.

Figure 5:
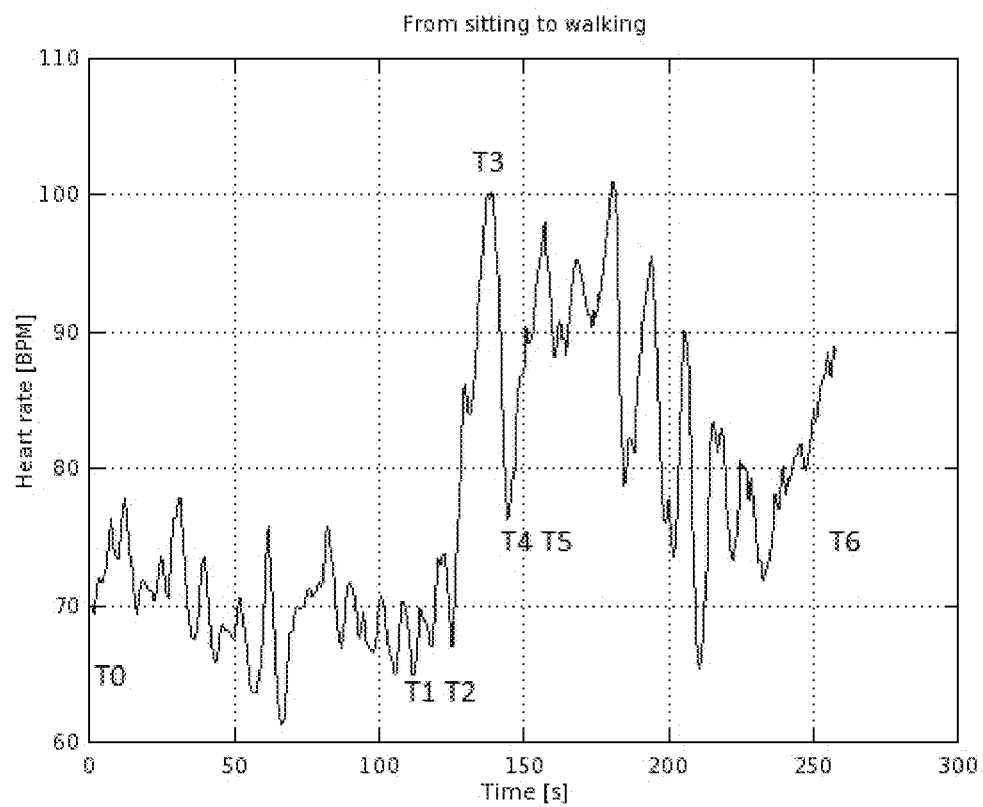
FIG. 5 is a graph of heart rate vs. time measured when a user transitions from sitting to walking.

In another example of measurement setup, a person uses a measurement device 100 in his finger. The person stands up (at time T1) from a seated position and begins walking. The accelerometer detects the provocation of standing up and initiates the HR/HRV measurement right away (FIG. 5). Since the bodily reaction is delayed from the physical provocation (of standing up at T1 to reaction at T2) the measurement device can detect and measure HR/HRV at the starting point (T1 to T2), the transients i.e. the $1^{st}$ (from down to peak, T2 to T3), $2^{nd}$ (from peak to down, T3 to T4), $3^{rd}$ (from down to peak, T4 to T5) and $n^{th}$ (T5 to T6, Tn to Tn+1) reaction of the body when it stabilises to a new homeostasis (walking). In one embodiment the measurement device is configured to have low power consuming functionalities such as a continuously active accelerometer (or other motion detection sensor). When the accelerometer detects motion (as at time T1 in FIG. 5) the measurement device starts to collect HR/HRV data. Since the bodily reaction (of HR/HRV) has a delayed response (in the graph one can see change at time T2) to actual movement, this arrangement enables capture of the HR/HRV of the person as it was before the provocation and also during and after the provocation. This enables power savings on the measurement device as well as computing resources savings such as in the memory of the measurement device since HR/HRV data is measured at the time of likely provocation based on movement detection.

Figure 6:
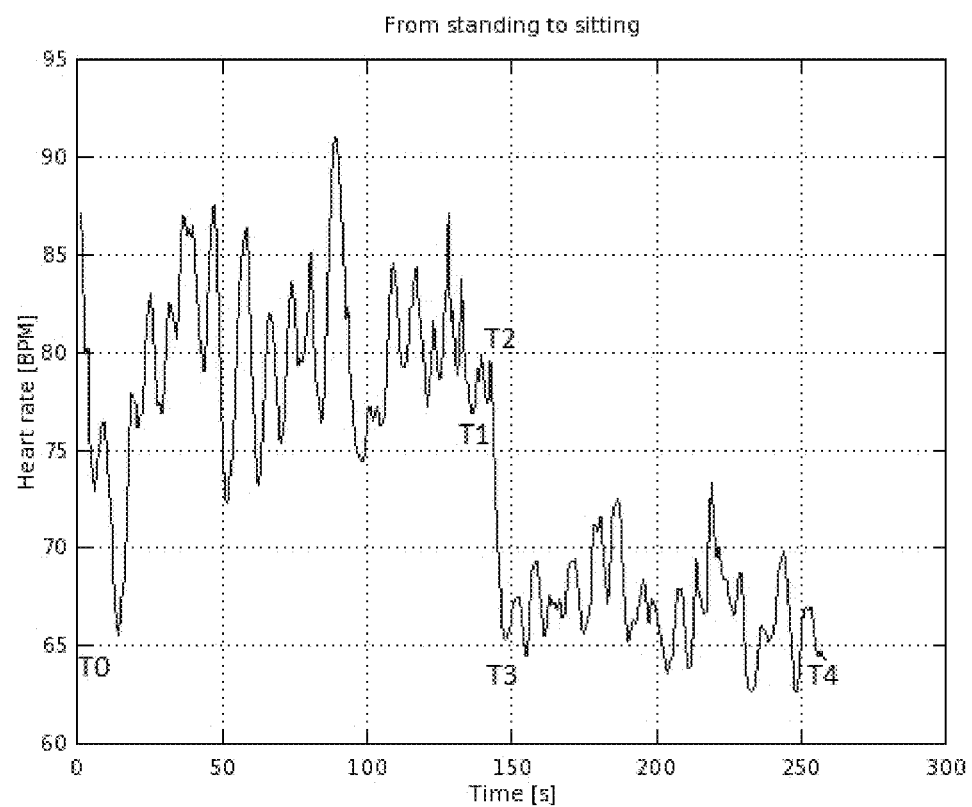
FIG. 6 is a graph of heart rate vs. time measured when a user transitions from standing to sitting.
Figure 7:
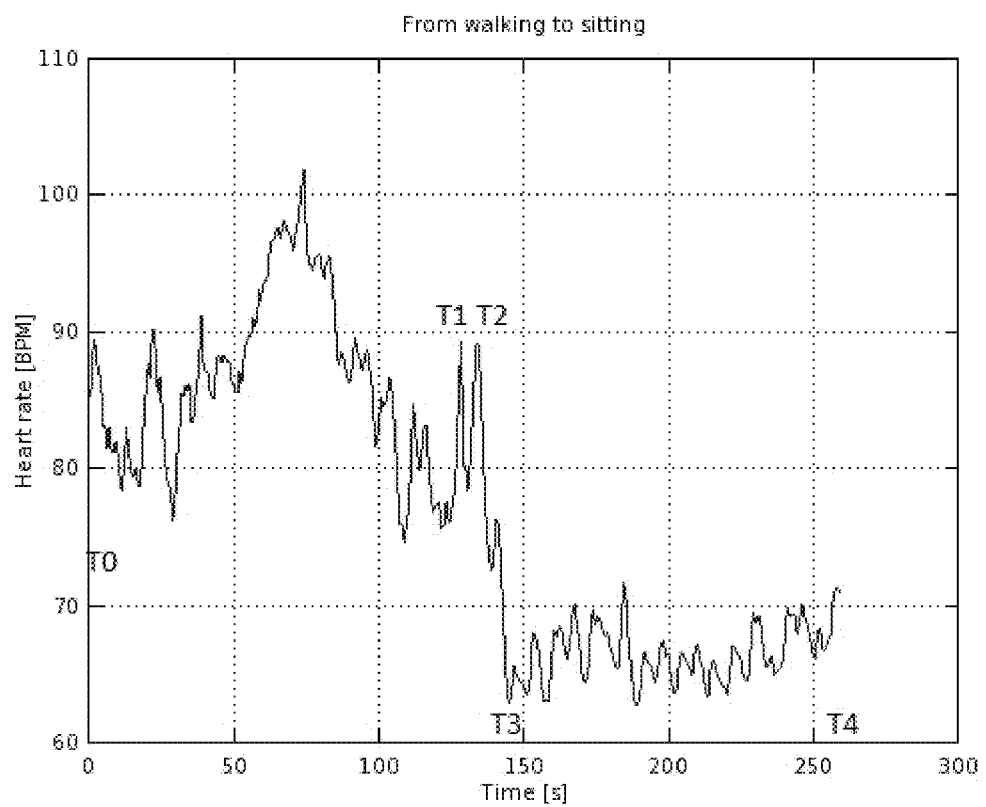
FIG. 7 is a graph of heart rate vs. time measured when a user transitions from walking to sitting.

A similar type of dynamic change or physical provocation i.e. measurable life event results when the person is standing or walking and sits down (FIGS. 6 & 7, respectively). Since the bodily reaction is again delayed from the physical state change (of sitting down, T1), the measurement device can detect and measure HR/HRV at the starting point (T1 to T2), the transients i.e. the $1^{st}$ (from peak to down, T2 to T3) and $n^{th}$ (Tn to Tn+1) reaction of the body when it stabilises to a new homeostasis (sitting). In one embodiment, the measurement device can be configured to switch on the HR/HRV data collection when the accelerometer data corresponds to change in motion of the person.

The reactions of the autonomic nervous system are measured and analysed during each phase. Both acute stress reaction and long term status of stress are analysed in ratio to the strength of provocation. When repeated measurements are executed over time the test results and analysis in each phase start to indicate the trend on e.g. how stress is developing over time and whether or not recovery is taking place.

A similar type of dynamic change or physical provocation i.e. measurable life event results when a person is standing or walking and sits down (FIGS. 6 and 7, respectively). Since the bodily reaction is again delayed from the physical state change (of sitting down, T1), the measurement device can detect and measure HR/HRV at the starting point (T1 to T2), the transients i.e. the $1^{st}$ (from peak to down, T1 to T2) and $n^{th}$ (Tn to Tn+1) reaction of the body, as well as bodily reactions during the recovery period after the activity has stabilised to a new level.

The reactions of the autonomic nervous system are measured and analysed during each phase. Both acute stress reaction and long term status of stress is analysed in ratio to the strength of provocation. When repeated measurements (in ratio to the provocation level) are executed over time the test results and analysis in each phase start to indicate the trend on e.g. how stress is developing over time and whether recovery is happening or not.

Figure 8:
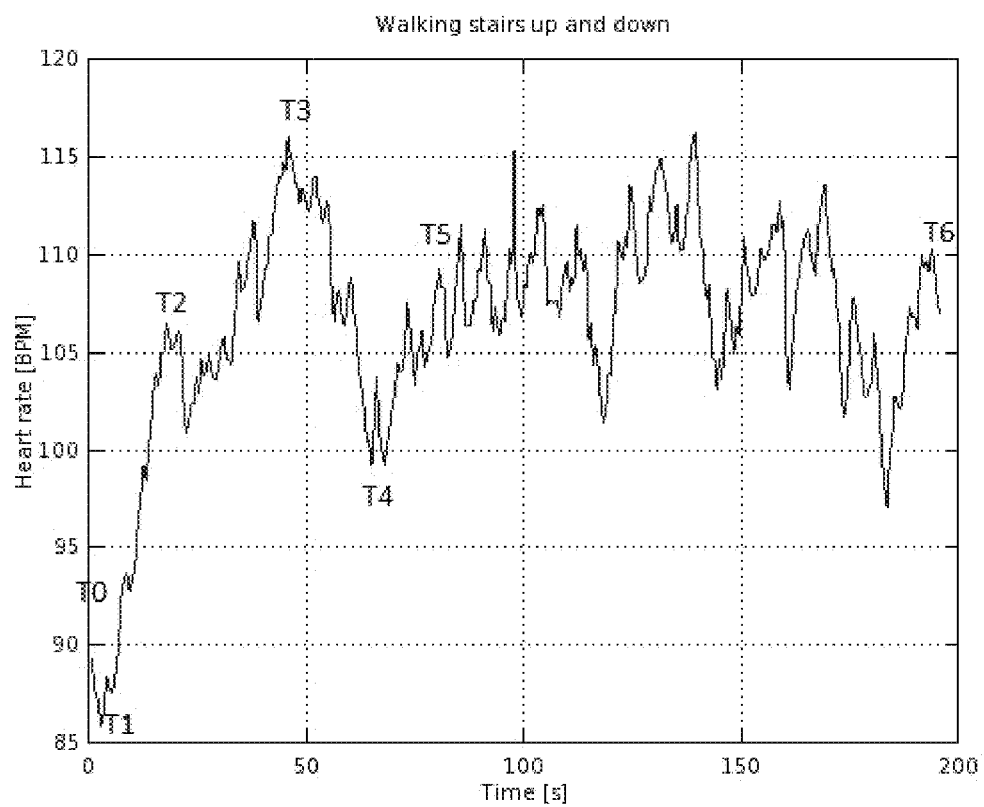
FIG. 8 is a graph of heart rate vs. time measured while a user walks stairs up and down.
Figure 9:
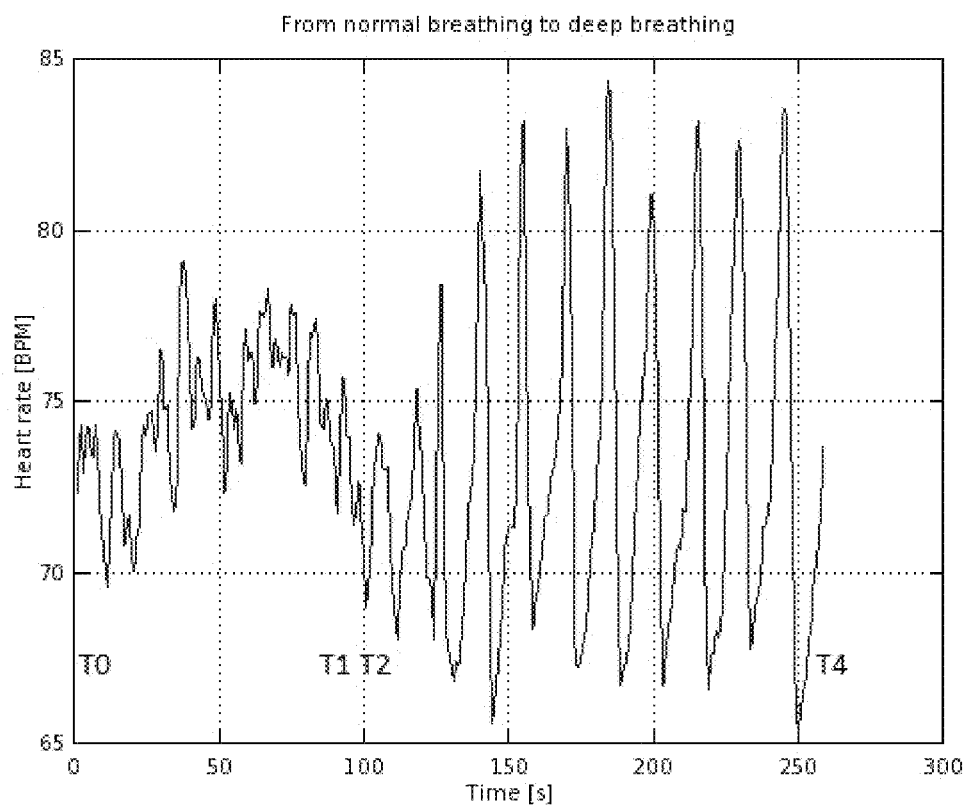
FIG. 9 is a graph of heart rate vs. time measured when a user transitions from normal breathing to deep breathing.

In another example of measurement setup a person uses a measurement device 100 on his finger. The person walks up and down stairs. The accelerometer detects the raise of activation i.e. the provocation of start walking the stairs up and initiates the HR/HRV measurement right away (FIG. 8). Since the bodily reaction is delayed from the physical provocation (of start climbing the stairs at T0 to first reaction at T1) the measurement device can detect and measure HR/HRV at the starting point (T0 to T1), the transients i.e. the $1^{st}$ (from down to peak, T2 to T3), $2^{nd}$ (from peak to down, T3 to T4), $3^{rd}$ (from down to peak, T4 to T5) and $n^{th}$ (T5 to T6, Tn to Tn+1) reaction of the body when it stabilises to a new homeostasis (walking).

In another example of measurement setup, a person again uses a measurement device 100 on his finger. The person starts a deep breathing exercise. The HR/HRV measurement is initiated by a coupled (mobile, PC etc.) application or other user action before the exercise begins. When the exercise begins at T1 (0.9) the device begins to detect and measure the bodily reactions in ratio of the respiration rate to the deepness change. The device and/or the coupled (mobile, PC etc.) application is arranged to indicate the breathing rhythm to the user based on fixed setting and/or measured data and may adjust in accordance with how the exercise proceeds i.e. based on the analysis of the measured data. The device and/or the coupled (mobile, PC etc.) application may indicate, in real-time, the proceeding of the exercise and the quality/level of bodily coherence (sympatho-vagal balance) reached by the user.

Additionally the device is configured to measure bodily reactions during exercise to detect stress levels and other bodily indications. If the deep breathing exercise progresses as the deep breathing test, the parasympathetic branch of the autonomic nervous system can be assessed. As those of ordinary skill in the art will appreciate, during the test the person breathes deeply and evenly, for example in a supine position, at six breaths per minute. To foster the compliance with the breathing rhythm, the coupled (mobile, PC etc.) application may display the rhythm for one minute.

Figure 10:
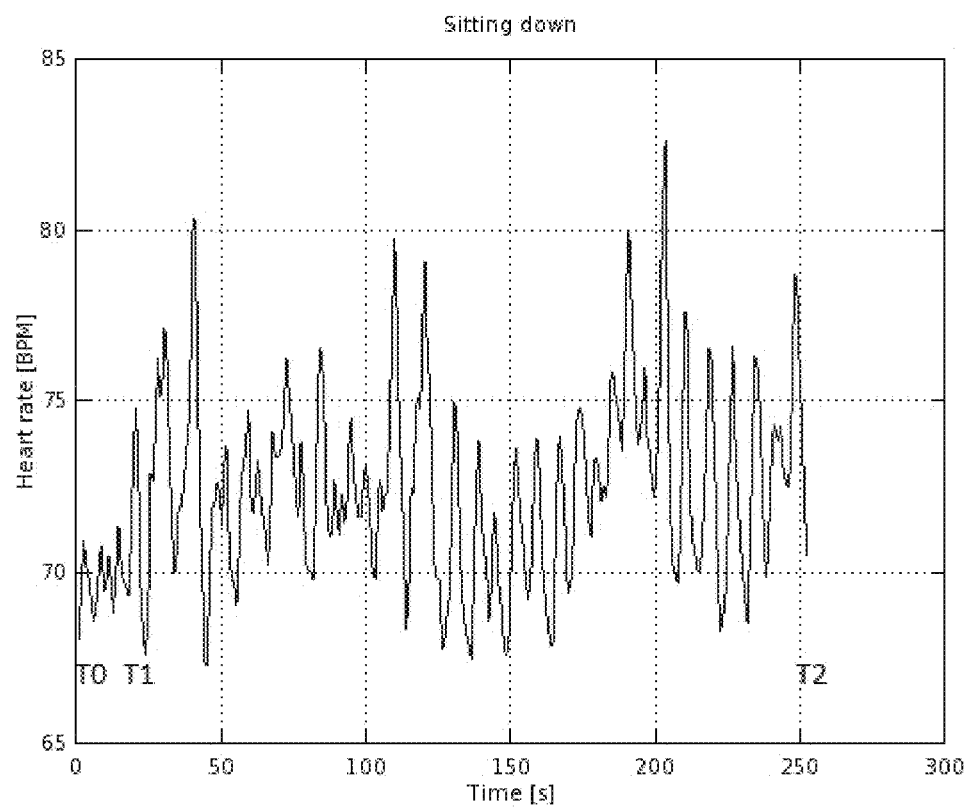
FIG. 10 is a graph of heart rate vs. time measured while a user is sitting down.
Figure 11:
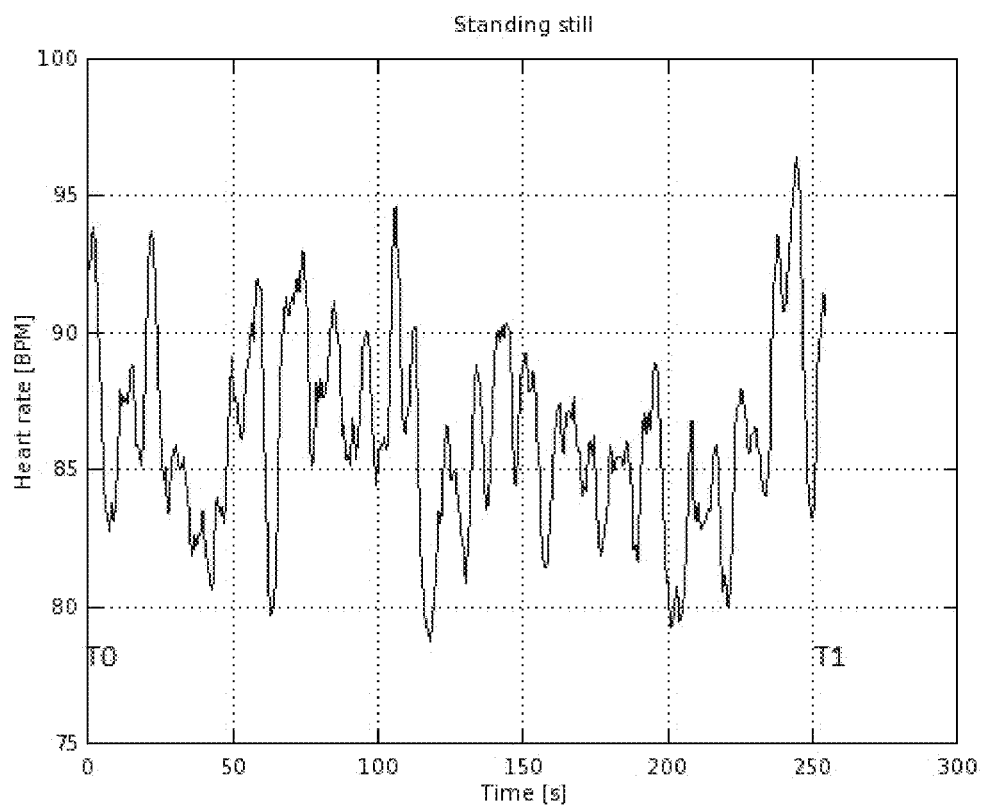
FIG. 11 is a graph of heart rate vs. time measured while a user is standing still.
Figure 12:
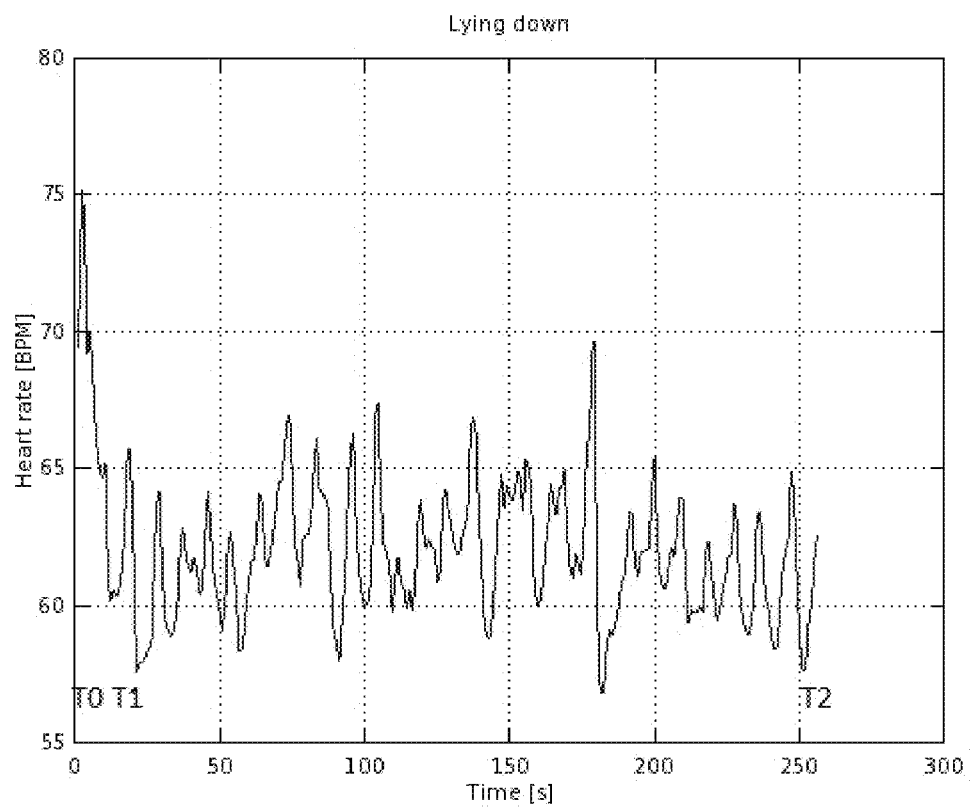
FIG. 12 is a graph of heart rate vs. time measured while a user is lying down.

In another yet example of measurement setup, a person again uses a measurement device 100 on his finger. The example is of non-provocation situation i.e. no transient physiological activation happens but the person is e.g. sitting, standing, laying down or otherwise in stationary activity state (FIGS. 10, 11 & 12). The HR/HRV measurement is initiated by a sniffing logic in the device, coupled (mobile, PC etc.) application or other user action. Based on the sniffing logic, the device takes samples of HR/HRV during the day both in provocative and non-provocative situations i.e. active and non-active situations. In this way the device is capable of detecting whether the ratio of HR and HRV compared to correlated activity is consistent i.e. in the healthy space mapped for the person.

If there is no activity, i.e. no physical provocation but HR is high, the person may potentially be acutely suffering e.g. from a mental, psychological or emotional stress or is having physiological stress reaction related to breathing (e.g. holding the breath) or other physiological stimulus like contraction, or a physiological stress reaction due to drinking or eating something that raises the pulse rate. When the device detects this kind of a situation it begins analyzing the situation from HRV and, additionally, may prompt the user to give subjective feedback on his/her emotional state (e.g. by raising his/her thumb up=>the device detects the movement and interprets the input accordingly). The user input is correlated with the measured data and stored in the long data. More detailed feedback and instructions may be provided to the user via the coupled (mobile, PC etc.) application in such a situation.

As described in above examples, the device is capable detecting transitional changes in the activity of a person (i.e. standing up, sitting down, climbing stairs etc.) and measuring the strength of provocation accordingly. Since the bodily reaction to provocation happens after a delay, measurement of HR/HRV can be initiated only when such provocation is detected and the whole phenomena and bodily reactions during each phase (before, during and after transition/provocation) are still able to be measured. This allows, among others, collection of data on bodily reactions in repetitive real-life situations i.e. measurable life events and formation a personal healthy space of values (3 dimensional space of HR, HRV, and activity/strength of provocation) that may be used as basis for providing prompt feedback as well as acute and long-term views and indications to the user. Also, it allows e.g. smart battery saving algorithms and other smart stand-alone features in the device.

The examples represent measurable life events where interdependence of HR and HRV may be examined and correlated with the level of activation or provocation, for example when HRV is too low compared to HR level or even when HR is separated i.e. too low compared to the level of activity or the level of provocation. With the device, these events may be detected and respective bodily reactions may be measured in real-time and thus the device is able to learn the 3-dimensional, personal healthy space of normal values. Thus, the system is self-learning and becomes the more accurate with continuous use.

In FIG. 2, an example 3-dimensional (3D) axis system is generally indicated by 20. The 3D axis system 20 includes an activity level axis 200, a HR axis 202, a HRV axis 204, a health space 206, and first and second health space projections 208 and 210. FIG. 2 will be described in conjunction with FIG. 1.

With reference to FIG. 1, measuring device 100 measures the HRV, the HR, and the corresponding activity level during different times of the day when a user is performing a variety of tasks. In addition to the HR, HRV, and the activity level estimates, measuring device 100 interprets user inputs with regard to the activity level and the types of stress the user is experiencing to arrive at various stress levels corresponding to different HR values and HRV values. Based on in-built algorithms measuring device 100 determines the combinations of the activity level, HR, and HRV values that are considered to be medically healthy. In an example, in a measurement scenario when the activity level is 'low' but the HRV is also 'low', measuring device 100 requests, from the user, an interpretation of whether the stress faced by the user is a 'positive stress' or a 'negative stress'. Measuring device 100 then accordingly labels the combination of the activity level, HR, and HRV values and saves the combination to historical data. In another example, when the HR value and the activity level are both detected as 'high' then measuring device 100 makes the interpretation of the physical activity as training as saves the time of day as the exercise time.

The healthy combinations of the activity level, HR, and HRV values hence obtained are plotted on the activity level axis 200, the HR axis 202, and the HRV axis 204, respectively to generate a 3D curve known as the health space 206. The health space 206 includes all the combinations of the activity level, HR, and HRV values that are considered to be medically healthy. When, during a subsequent measurement, measuring device 100 detects deviations in the measured values of the activity level, HR, and HRV from the values in the health space 206, measuring device 100 may perform at least one of the following: provide haptic and/or visual feedback to the user—to stimulate user action, request user input regarding how he/she is feeling, viz., by asking the user to make a 'thumbs-up' gesture (i.e., to tilt a accelerometer sensor of the measuring device 100) response if feeling good, and activate connection to the mobile terminal 104 to activate an application.

Additional examples of the various combinations of the values of HR and the activity level are listed in the below Table I, II, and III:

TABLE I

| HR | Activity | Indication/resulting action |
|---|---|---|
| Low | High | Potentially an indication of sympathetic or parasympathetic overreaching state where body is not reacting normally to the raised activity level if the pulse rate is outside the normal limits for the person compared to long term levels |
| Low | Low | Potentially a normal relaxed situation if the pulse rate is within the normal limits for the person compared to long term levels |
| High | Low | Potentially a mental, psychological or emotional stress reaction or a physiological stress reaction related to breathing (holding the breath) or other physiological stimulus like contraction or a physiological stress reaction to eating or drinking something that raises the pulse rate |
| High | High | Potentially a normal bodily reaction to raised activity if the pulse rate is within the normal limits for the person compared to long term levels |

TABLE II

| HR | HRV | Activity | Indication/resulting action |
|---|---|---|---|
| Low | Low | High | Potentially an indication of sympathetic or parasympathetic overreaching state where body is not reacting normally to the raised activity level if the pulse rate is outside the normal limits for the person compared to long term levels |
| Low | High | Low | Potentially a mental, psychological or emotional stress reaction or a physiological stress reaction related to breathing (holding the breath) or other physiological stimulus like contraction or a physiological stress reaction to eating or drinking something that raises the pulse rate |
| Low | High | High | Potentially an indication of sympathetic or parasympathetic overreaching state where body is not reacting normally to the raised activity level if the pulse rate is outside the normal limits for the person compared to long term levels |
| High | Low | Low | Potentially a mental, psychological or emotional stress reaction or a physiological stress reaction related to breathing (holding the breath) or other physiological stimulus like contraction or a physiological stress reaction to eating or drinking something that raises the pulse rate |
| High | Low | High | Potentially a normal bodily reaction to raised activity if the pulse rate is within the normal limits for the person compared to long term levels |
| High | High | Low | Potentially a mental, psychological or emotional stress reaction or a physiological stress reaction related to breathing (holding the breath) or other physiological stimulus like contraction or a physiological stress reaction to eating or drinking something that raises the pulse rate |
| High | High | High | Potentially a normal bodily reaction to raised activity if the pulse rate is within the normal limits for the person compared to long term levels |

TABLE III

| HR | HRV | Provocation | Indication/resulting action |
|---|---|---|---|
| Low | Low | High | please refer the above Table II |
| Low | High | Low | please refer the above Table II |
| Low | High | High | please refer the above Table II |
| High | Low | Low | please refer the above Table II |
| High | Low | High | please refer the above Table II |
| High | High | Low | please refer the above Table II |
| High | High | High | please refer the above Table II |

Figure 13:
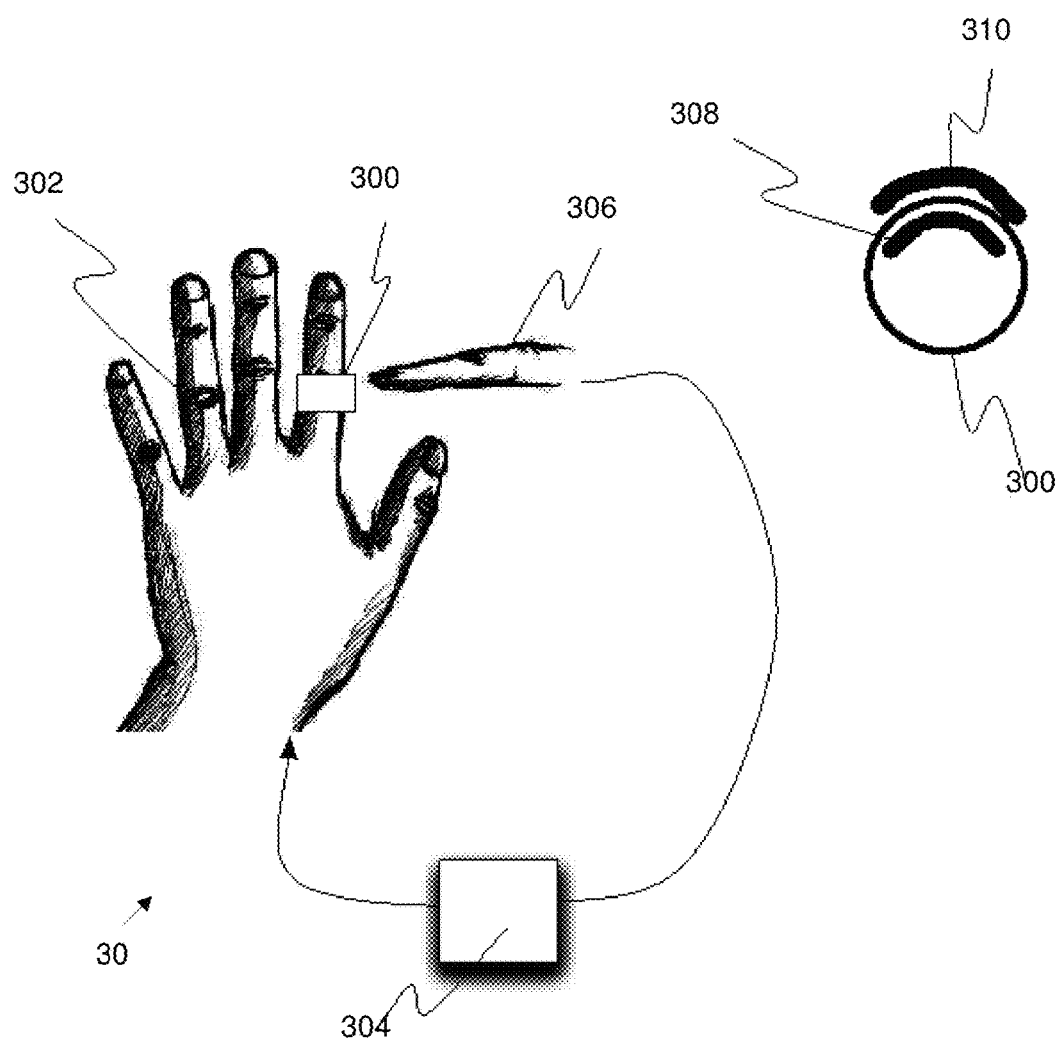
FIG. 13 is an illustration of an example arrangement of the apparatus for measuring the orthostatic HR to generate Electrocardiogram (ECG)

In FIG. 13, an example apparatus is indicated generally by 30. The apparatus 30 includes a measuring device 300, a firsthand 302, a heart 304 (depicted schematically), and a second hand 306. The measuring device 300 includes first and second electrodes 308 and 310.

The example measuring device 300 may be formed as a ring and used to generate an ECG of the user wearing the measuring device 300 in a finger of the first hand 302. Measuring device 300 includes first and second electrodes 308 and 310 positioned on an inside and an outside surface of the measuring device 300, respectively. To generate the ECG, with the measuring device 300 worn on the finger of the first hand 302 and a mode of the measuring device set to ECG mode, the user may touch the measuring device 300 with a finger of the second hand 306. Touching the measuring device 300 with the finger of the second hand 306 results in the formation of a loop from the finger of the first hand 302 to the finger of the second hand 306 via the heart 304. Subsequent to the formation of the loop, the measuring device 300 generates the ECG.

Figure 14:
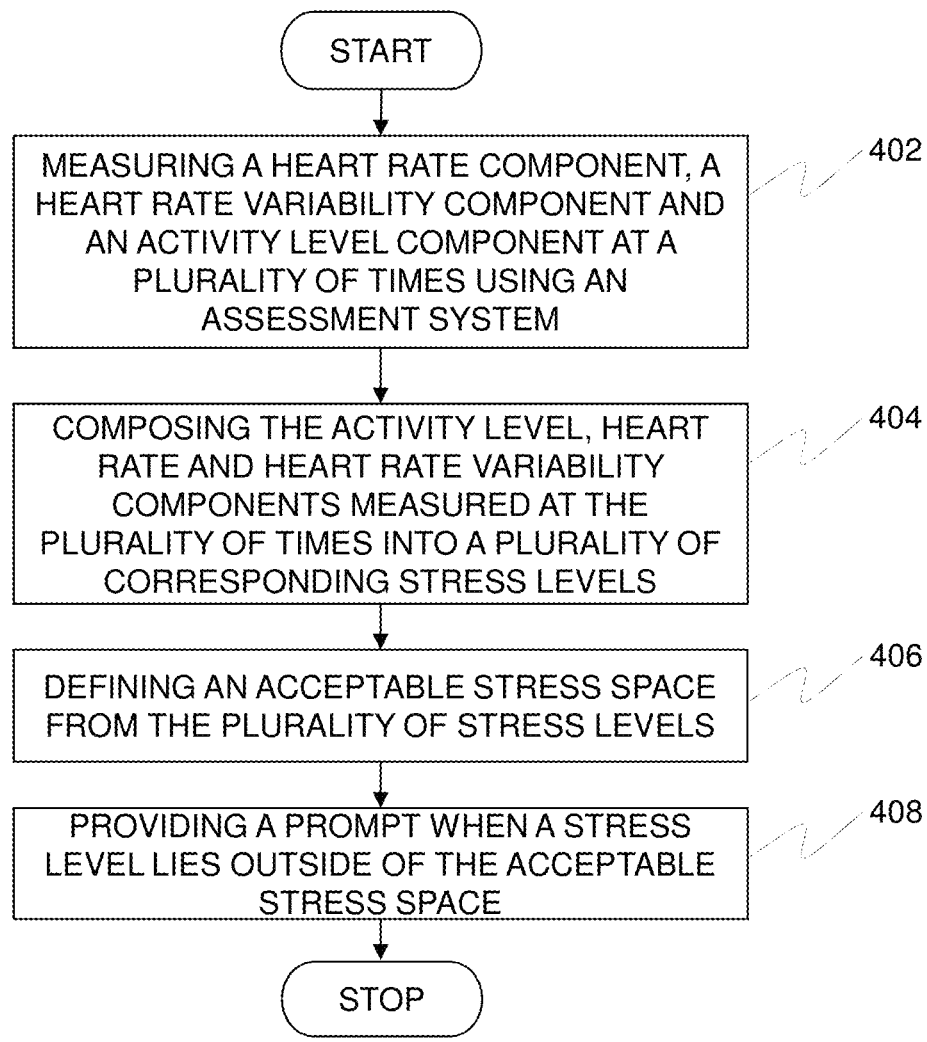
FIG. 14 is an illustration of steps of an example method for measuring stress.

In FIG. 14, steps of an example method for measuring stress using apparatus 30 are illustrated. FIG. 14 is explained in detail in conjunction with FIGS. 1, 2, and 13.

In a first step 402, a HR value, a HRV value, and an activity level value are measured at various times during the day when the user is either lying relaxed in a supine position or performing activities with different levels of exertion. For example, the user may be training in a gym, climbing stairs, working on a computer, or similar. The measurement of the HR value, HRV value, and the activity level value is performed using an assessment system that can include the measuring device 100, the mobile terminal 104, the communication network 106, the server 108, and the database 110. The measurement of the HR value, HRV value, and the activity level value has been explained in detail in conjunction with FIG. 1.

In a step 404, the various measured values corresponding to HR, HRV, and activity level obtained at a plurality of times are composed into a plurality of corresponding stress levels. As described in detail in conjunction with FIG. 1, measuring device 100 sends the measured data to mobile terminal 104 and from mobile terminal 104 via communication network 106 to server 108 for further processing. Server 108 processes, analyses, and correlates the measured data to output stress levels experienced by the user and stores the processed data in database 110 for future comparisons. Alternatively the data can be processed and analyzed locally in measuring device 100 or at mobile terminal 104.

In an embodiment of the present disclosure, server 108 analyses the measured data using a sliding correlation method. In an embodiment of the present disclosure, as a stand-alone device measuring device 100 has data processing power, built-in algorithms and other necessary capabilities to execute automated and dynamic orthostatic test procedures (either from supine to standing or from sitting to standing) to measure whole ANS functionality i.e. sympathovagal resources (stress reactions vs. recovery). Measuring device 100 processes, analyses, and correlates the measured data using sliding correlation method. Measuring device 100 provides haptic and visual instructions to the user during the execution of the orthostatic test to receive user inputs regarding the activity level and stress type that the user is experiencing.

In step 406, an acceptable stress space is defined based on the plurality of stress levels obtained based on interpretation of the orthostatic test results such as the values of the HR, HRV, and the activity levels. As explained in detail in conjunction with FIGS. 1 and 2, measuring device 100 in addition to the HR, HRV, and the activity level estimates, measuring device 100 interprets user inputs with regard to the activity level and the types of stress the user is experiencing to arrive at various stress levels corresponding to different HR values and HRV values. Based on in-built algorithms and processing by server 108 measuring device 100 determines the combinations of the activity level, HR, and HRV values that are considered to be medically healthy. The healthy combinations of the activity level, HR, and HRV values hence obtained are plotted on activity level axis 200, HR axis 202, and HRV axis 204, respectively to generate a 3D curve known as the health space 206. Health space 206 includes all the combinations of the activity level, HR, and HRV values that are considered to be medically healthy.

In step 408, a prompt is provided to the user when a stress level lies outside of the acceptable stress space, that is, outside of health space 206. The prompt is provided to the user by measuring device 100. In an embodiment of the present disclosure, when measuring device 100 detects a stress level outside the acceptable limits, measuring device 100 may perform at least one of the following: provide haptic and/or visual feedback to the user to activate user action, request for the user input on how he/she is feeling, viz., by asking the user to make a thumbs-up gesture (i.e., to tilt a accelerometer sensor of measuring device 100) as a response if feeling good, and activate connection to mobile terminal 104 to activate an application.

Figure 15:
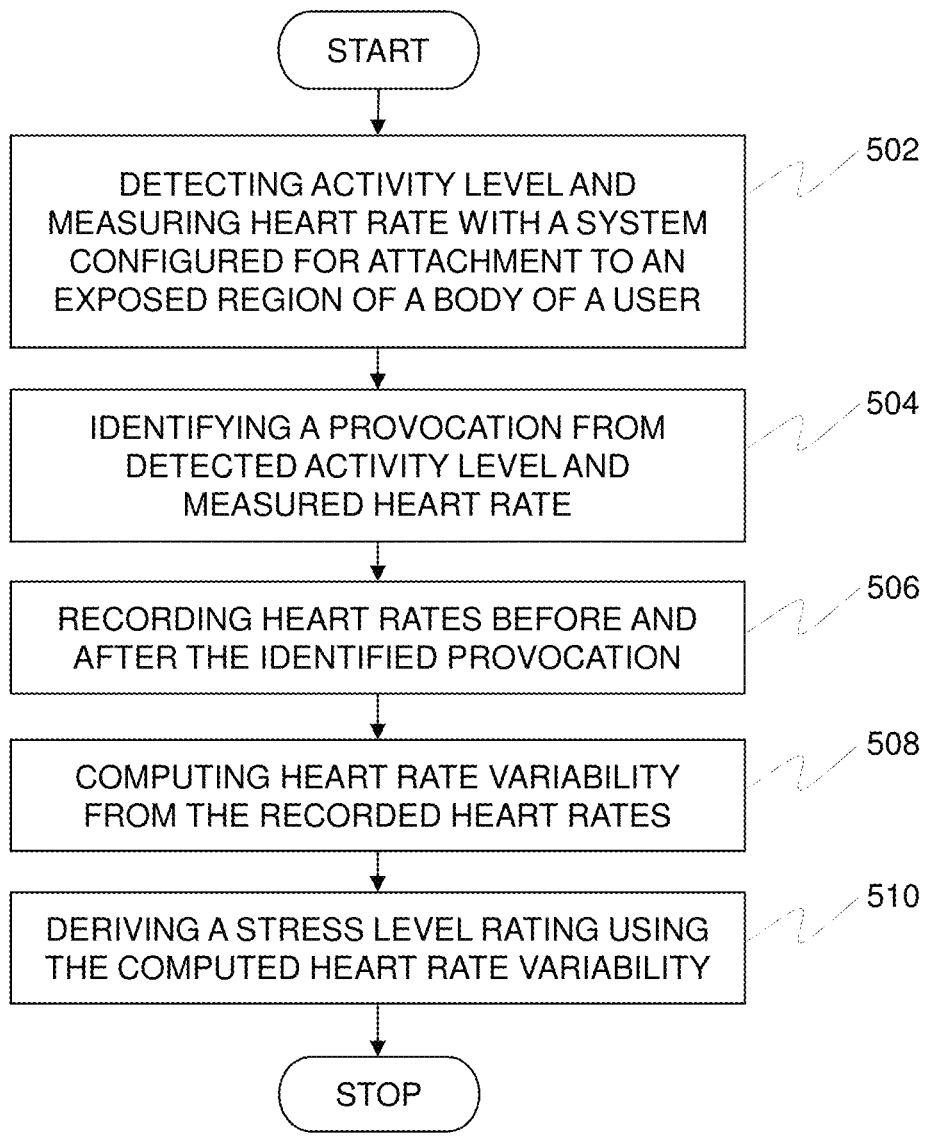
FIG. 15 is an illustration of steps of another example method for measuring stress.

In FIG. 15, steps of an example method for measuring stress using the apparatus 10 are illustrated. FIG. 15 is explained in detail in conjunction with FIGS. 1, 2, and 13.

In step 502, an activity level and a HR are detected with a system configured to be attached to an exposed region of a body of a user. The system used for detecting the activity level and the HR is measuring device 100. Measuring device 100 is attached to the exposed region of the body of the user, typically to a forefinger of one of the hands.

In step 504, a provocation experienced by the user's body is identified. Measuring device 100 is equipped with one or more sensors, viz., accelerometer, a gyroscope, and a magnetometer for measuring the disposition of the user, the strength of movement of the user, etc. to judge the activity level of the user. Measuring device 100 also interprets user input to understand and verify the activity level that the user is being subjected to. The procedure followed by measuring device 100 for accepting user input and incorporating the user input into judging the activity level of the user has been described in detail in conjunction with FIGS. 1 and 2.

In step 506, the HR is measured before and after identifying a provocation by the measuring device 100 in a manner described in conjunction with FIGS. 1 and 2. In an embodiment of the present disclosure, the plethysmogram (i.e., imaging of a change in blood volume in the body part to which the measuring device 100 is attached) is rendered by one or more of a transmissive LED or a transflective LED. In an embodiment of the present disclosure, an ECG may also be generated in addition to detecting the HR of the user as described in conjunction with FIG. 13. The duration of measurement of the HR before and after the provocation is automatically adjusted based on the signal quality etc. during a measurement test. The measurement criteria followed by measuring device 100 have been described in detail in conjunction with FIGS. 1 and 2.

In step 508, a HRV value is computed using the HR values obtained before and after the provocation as described in conjunction with FIGS. 1 and 2. In step 510, a stress level rating is derived from the HRV value calculated above. The stress level rating is derived from correlating HRV values obtained at various times of the day when the user is having various activity levels with those of the activity levels. The estimation of stress levels also includes taking visual and/or haptic feedback from the user to refine the estimates of stress levels as described in conjunction with FIGS. 1 and 2.

Figure 16:
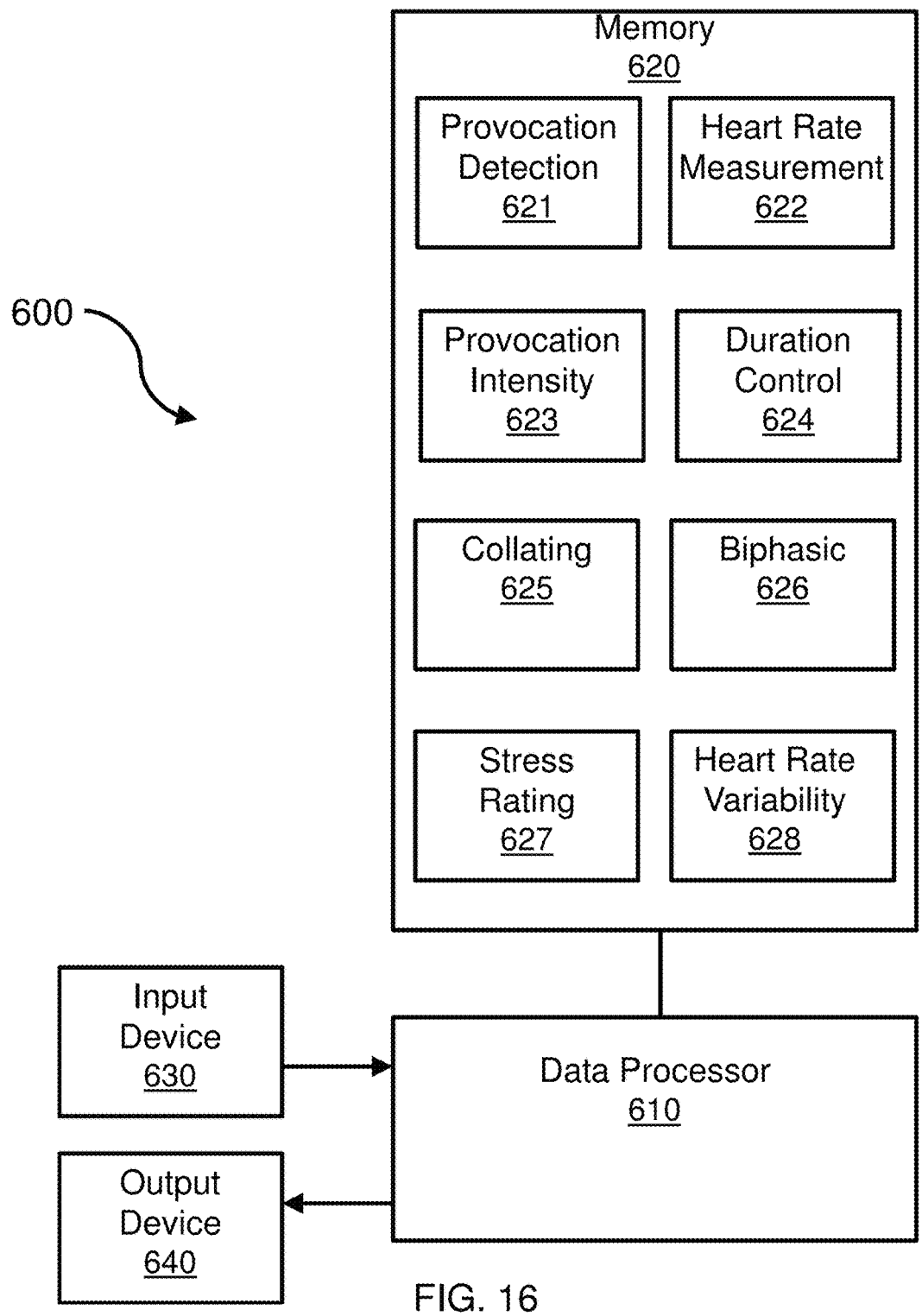
FIG. 16 is an illustration of an example system for measuring stress.

In FIG. 16, an example assessment apparatus is indicated generally by 600. The assessment system 600 includes a data processor 610, a memory 620, a provocation detection module 621, a HR measurement module 622, a provocation intensity module 623, a duration control module 624, a collating module 625, a biphasic module 626, a stress rating module 627, a HRV module 628, input devices 630, and output devices 640.

The input devices 630 are used for measuring at least one of the HR, HRV, activity level, and provocation level. The input devices 630 are substantially similar to measuring devices 100 or 300 and the output devices 640 may include any of a variety of output devices including but not limited to mobile terminal 104, printers, displays and audio speakers.

The data processor 610 processes measurement data generated based on the measurements performed by input devices 630. Data processor 610 may be a component of a mobile terminal or a server system or may be a node in a communications network. Memory 620 may also be a component of a mobile terminal or a sever system or may be a node in a communications network. In some examples, data processor 610 and memory 620 may be components of the apparatus 10 (FIG. 1).

Provocation detection module 621 is configured to record provocations, heart rate measurement module 622 is configured to record heart rates, heart rate variability module 628 is configured to compute heart rate variability by combining heart rate before and after a provocation detected by the detection module and stress rating module 627 is configured to derive or compose a stress level rating from the heart rate variability recorded or otherwise stored in or on the memory 620.

Provocation detection module 621 is further configured to indicate a provocation in response to measuring both a high HR and a low activity level, in response to detecting a low activity level and a low HRV and in response to measuring a high HR and a high activity level.

Duration control module 624 may also be stored within memory 620 and is configured to vary the times before and after a provocation at which the HR measurement module records heart rates. Duration control module 624 may be arranged as a sub-component of the heart rate variability module 628 or may exist as an independent module.

Provocation intensity module 623 may also be stored within memory 620 and is configured to record and pair an intensity to detected provocations. Provocation intensity module 623 may be arranged as a sub-component of the provocation detection module or may exist as an independent module.

Collating module 625 is configured to compare at least one of HR, HRV, stress level rating and provocation intensity for a plurality of provocations to correlate provocations of similar type. Collating module 625 is further configured to analyze at least one of HR, HRV, stress level and provocation with a sliding autocorrelation method. Further, biphasic module 626 is configured to record biphasic heart rate response after a provocation.

The various modules of assessment system 600 may be arranged differently than illustrated. Some modules may be eliminated, some may be added and some modules may be subcomponents or super components of one another.

In one embodiment some or all of the components of assessment system 600 may be integrated in measurement device 100 (FIG. 1).

Modifications to embodiments of the disclosure described in the foregoing are possible without departing from the scope of the disclosure as defined by the accompanying claims. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. A method for measuring stress, comprising:
   with an assessment system at each of a plurality of times, recording a heart rate, a heart rate variability and an activity level;
   for each of the plurality of times, composing the recorded heart rate, heart rate variability and activity level into a corresponding stress level;
   forming, from the plurality of stress levels, a three-dimensional health space defining acceptable stress level limits;
   with the assessment system, recording a current heart rate, a current heart rate variability and a current activity level;
   composing the recorded current heart rate, current heart rate variability and current activity level into a corresponding current stress level; and
   providing a prompt when the current stress level lies outside of the three-dimensional health space.

2. The method as set forth in claim 1, wherein providing a prompt further comprises providing an alert.

3. The method as set forth in claim 1, wherein providing a prompt further comprises requesting user input regarding a disposition associated with the stress level.

4. The method as set forth in claim 3, further comprising receiving the user input regarding the disposition.

5. The method as set forth in claim 4, further comprising correlating the input regarding the disposition with stress levels.

6. The method as set forth in claim 1, wherein recording the activity level further comprises detecting motion with one or more of an accelerometer and a gyroscope.

7. The method as set forth in claim 1, wherein recording the heart rate further comprises using one or more of a photoplethysmogram and an electrocardiogram.

8. The method as set forth in claim 1, wherein recording the heart rate variability further comprises computing the heart rate variability using the measured heart rate.

9. The method as set forth in claim 1, wherein composing the activity level, the heart rate and the heart rate variability into a corresponding stress level further comprises using one or more of a mobile terminal, a server system, a database and a communications network.

10. The method as set forth in claim 1, wherein recording heart rate variability further comprises recording heart rate variability in response to a sudden increase in the activity level component.

11. A method of measuring stress, comprising:
    detecting activity level and measuring heart rate with a system configured for attachment to an exposed region of a body of a user;
    identifying a provocation from detected activity level and measured heart rate;
    recording heart rates before and after the identified provocation;
    computing heart rate variability from the recorded heart rates; and
    using the activity level, heart rate and heart rate variability to form, a three-dimensional health space defining acceptable stress level limits.

12. The method as set forth in claim 11, further comprising recording a biphasic heart rate response after the provocation.

13. The method as set forth in claim 11, wherein identifying the provocation further comprises measuring a high heart rate and detecting a low activity level.

14. The method as set forth in claim 11, further comprising prompting a user for a disposition input when detected activity level is low and computed heart rate variability is low.

15. The method as set forth in claim 11, further comprising establishing a type of the provocation to be a training activity when measured heart rate is high and detected activity level is high.

16. A method of measuring stress, comprising:
   detecting provocations and measuring heart rate with a system configured for attachment to an exposed region of a body of a user;
   with a data processor, computing heart rate variability by combining heart rate measured for a duration before a detected provocation with heart rate measured for a duration after the detected provocation;
   deriving a stress level rating using the computed heart rate variability; and
   comparing the stress level rating to a three-dimensional health space defining acceptable stress level limits.

17. The method as set forth in claim 16, wherein both the duration before the provocation and the duration after the provocation are adjustable.

18. The method as set forth in claim 16, further comprising establishing provocation intensity for each detected provocation.

19. The method as set forth in claim 18, further comprising comparing values of at least one of heart rate, heart rate variability, stress level rating and provocation intensity for a plurality of provocations to correlate provocations of similar type.

20. The method as set forth in claim 19, wherein comparing comprises analyzing with a sliding autocorrelation method.

* * * * *